(12) United States Patent
Renne et al.

(10) Patent No.: US 11,207,154 B2
(45) Date of Patent: Dec. 28, 2021

(54) IRRIGATED SURGICAL GUIDES AND METHODS OF MANUFACTURING THE SAME

(71) Applicant: MUSC Foundation for Research Development, Charleston, SC (US)

(72) Inventors: Walter Renne, Charleston, SC (US); Zachary Evans, Johns Island, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 16/469,811

(22) PCT Filed: Mar. 12, 2019

(86) PCT No.: PCT/US2019/021749
§ 371 (c)(1),
(2) Date: Jun. 14, 2019

(87) PCT Pub. No.: WO2019/178022
PCT Pub. Date: Sep. 19, 2019

(65) Prior Publication Data
US 2021/0000568 A1 Jan. 7, 2021

Related U.S. Application Data

(60) Provisional application No. 62/682,489, filed on Jun. 8, 2018, provisional application No. 62/641,821, filed on Mar. 12, 2018.

(51) Int. Cl.
*A61C 1/08* (2006.01)
*B33Y 80/00* (2015.01)
(Continued)

(52) U.S. Cl.
CPC ............. *A61C 1/084* (2013.01); *A61B 17/17* (2013.01); *A61B 18/201* (2013.01); *A61B 34/10* (2016.02);
(Continued)

(58) Field of Classification Search
CPC ........... A61C 1/084; A61C 3/02; A61C 17/02; A61C 13/0004; A61C 19/04;
(Continued)

(56) References Cited

U.S. PATENT DOCUMENTS 5,468,239 A 11/1995 Tanner
5,641,287 A 6/1997 Gittleman
(Continued)

OTHER PUBLICATIONS

Albrektsson T, Branemark PI, Hansson HA, Lindstrom J. Osseointegrated titanium implants. Requirements for ensuring a long-lasting, direct bone-to-implant anchorage in man. Acta Orthop Scand 1981;52:155-70.
(Continued)

*Primary Examiner* — Moshe Wilensky
*Assistant Examiner* — Kyle A Cook
(74) *Attorney, Agent, or Firm* — Riverside Law LLP

(57) ABSTRACT

Provided herein are surgical guides with internal channels for irrigation cooling. In one embodiment, an apparatus for guiding a surgical instrument includes a proximal side and a distal side. A first channel is configured to guide a material removal device, where the first channel extends from the proximal side of the apparatus to the distal side of the apparatus. A second channel configured to direct irrigation fluid, where the second channel extends from the proximal side of the of the apparatus to the distal side of the apparatus. The first channel is separate from the second channel. A method of performing a surgical procedure and a method of manufacturing a surgical guide are also disclosed. In certain
(Continued)

embodiments, the surgical guides may be manufactured via additive manufacturing processes, including for example, three-dimensional printing processes.

15 Claims, 25 Drawing Sheets

(51) Int. Cl.

| | | |
|---|---|---|
| A61C 8/00 | (2006.01) | |
| A61B 17/17 | (2006.01) | |
| A61C 9/00 | (2006.01) | |
| B33Y 10/00 | (2015.01) | |
| B33Y 50/02 | (2015.01) | |
| A61B 34/10 | (2016.01) | |
| B29C 64/10 | (2017.01) | |
| A61B 18/20 | (2006.01) | |
| A61C 1/00 | (2006.01) | |
| G06T 13/20 | (2011.01) | |
| A61C 3/02 | (2006.01) | |
| A61B 17/16 | (2006.01) | |
| G06T 1/00 | (2006.01) | |

(52) U.S. Cl.
CPC .......... A61C 1/0069 (2013.01); A61C 8/0089 (2013.01); A61C 9/004 (2013.01); B29C 64/10 (2017.08); B33Y 10/00 (2014.12); B33Y 50/02 (2014.12); B33Y 80/00 (2014.12); G06T 13/20 (2013.01); *A61B 2017/1651* (2013.01); *A61B 2034/108* (2016.02); *A61C 3/02* (2013.01); *G06T 1/0007* (2013.01)

(58) Field of Classification Search
CPC ..... A61C 1/0069; A61C 8/0089; A61C 9/004; B33Y 10/00; B33Y 50/02; B33Y 80/00; B29C 64/10; G06T 1/0007; G06T 13/20; A61B 34/10; A61B 18/201; A61B 17/17; A61B 2017/1651; A61B 2034/108; A61B 2217/005; A61B 2217/007
See application file for complete search history.

(56) References Cited

U.S. PATENT DOCUMENTS

| | | |
|---|---|---|
| 5,688,283 A | 11/1997 | Knapp |
| 8,282,638 B2 | 10/2012 | Choe et al. |
| 8,543,234 B2 | 9/2013 | Gao |
| 8,915,921 B2 | 12/2014 | Ralph et al. |
| 9,283,055 B2 | 3/2016 | Thompson, Jr. et al. |
| 2010/0256649 A1 | 10/2010 | Capsal |
| 2013/0218163 A1 | 8/2013 | Frey |
| 2017/0071697 A1 | 3/2017 | Groscurth |
| 2017/0319217 A1 | 11/2017 | Manley |
| 2019/0274785 A1* | 9/2019 | Renne .................... A61B 34/10 |

OTHER PUBLICATIONS

Eriksson RA, Adell R. Temperatures during drilling for the placement of implants using the osseointegration technique. J Oral Maxillofac Surg 1986;44:4-7.

Kerawala CJ, Martin IC, Allan W, Williams ED. The effects of operator technique and bur design on temperature during osseous preparation for osteosynthesis self-tapping screws. Oral Surg Oral Med Oral Pathol Oral Radiol Endod 1999;88:145-50.

Harris BH, Kohles SS. Effects of mechanical and thermal fatigue on dental drill performance. Int J Oral Maxillofac Implants 2001;16:819-26.

Sener BC, Dergin G, Gursoy B, Kelesoglu E, Slih I. Effects of irrigation temperature on heat control in vitro at different drilling depths. Clin Oral Implants Res 2009;20:294-8.

Sharawy M, Misch CE, Weller N, et al: Heat generation during implant drilling: The significance of motor speed. J Oral Maxillofac Surg 60:1160, 2002.

Scott ESE Bulloch. Comparison of heat generation between internally guided (cannulated) single drill and traditional sequential drilling with and without a drill guide for dental implants. The International journal of oral & maxillofacial implants 27(6) Nov.-Dec. 2012 1942-4434.

Misir AF, Sumer M, Yenisey M, Ergioglu E. Effect of surgical drill guide on heat generated from implant drilling. J Oral Maxillofac Surg 2009;67:2663-8.

Davidson SR, James DF: Measurement of thermal conductivity of bovine cortical bone. Med Eng Phys 22:741, 2000.

Soldatos, N et al: Temperature changes during implant osteotomies utilizing 3 different implant systems. The Journal of Implant and Advanced Clinical Dentistry 8(6), Nov. 2016.

Mishra SK, Chowdhary R:Heat Generated by Dental Implant Drills During Osteotomy—A Review J Indian Prosthodont Soc Jun. 2014; 14(2): 131-143.

* cited by examiner

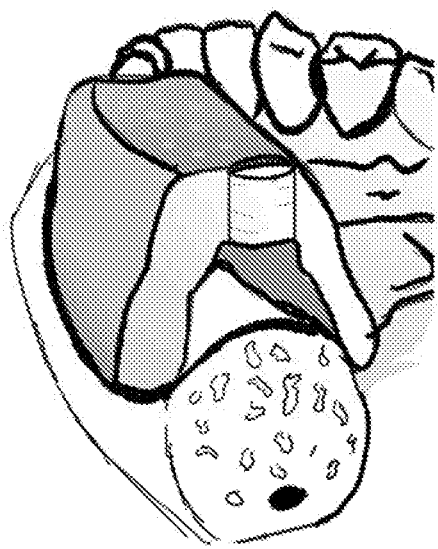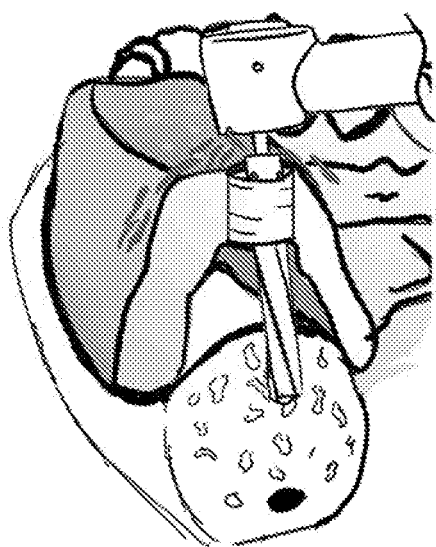
FIG. 14A
(Prior Art)
FIG. 14B
(Prior Art)

| Group | Comparison | P-value |
|---|---|---|
| Drill 1 | Control vs Experiment | 0.0002 |
| Drill 2 | Control vs Experiment | 0.1715 |
| Thermal | Control vs Experiment | 0.0142 |

Table 1: *p-value analysis of Experimental v. Control for change in bone temperature and change in drill temperature*

FIG. 18

| Position | Group | N | Mean | Median | Std Dev | Minimum | Maximum |
|---|---|---|---|---|---|---|---|
| Drill 1 | Control | 10 | 25.54 | 21.20 | 15.33 | 9.80 | 63.20 |
|  | EXP | 10 | 7.13 | 5.15 | 5.89 | 2.20 | 18.80 |
| Drill 2 | Control | 7 | 14.14 | 10.50 | 10.53 | 3.50 | 33.90 |
|  | EXP | 8 | 3.70 | 2.70 | 3.42 | 0.20 | 9.60 |
| Thermal | Control | 10 | 17.20 | 17.70 | 7.76 | 2.30 | 33.80 |
|  | EXP | 10 | 4.18 | 2.40 | 4.94 | -1.30 | 10.50 |

Table 2: *Mean, Median, and Standard Deviation of Temperature change in Bone and Osteotomy drill*

FIG. 19

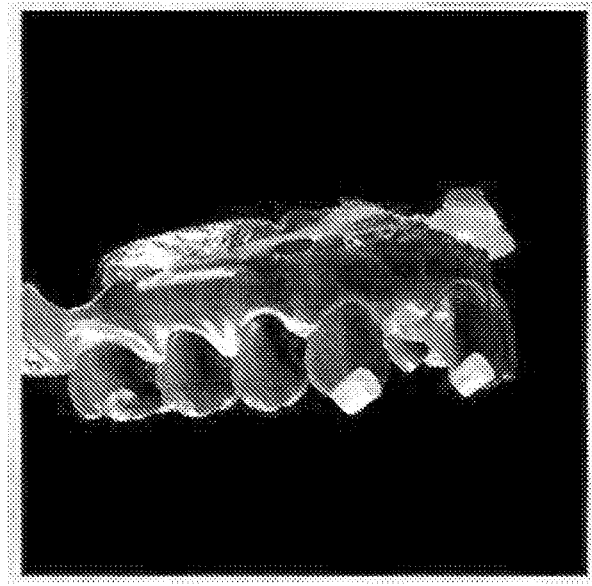 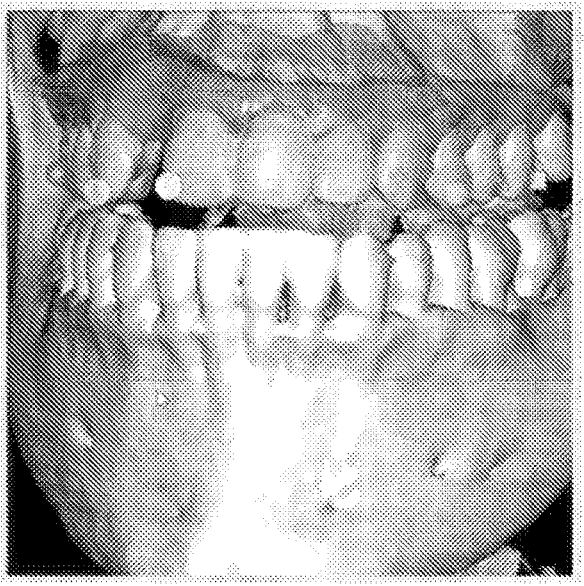
FIG. 25A   FIG. 25B
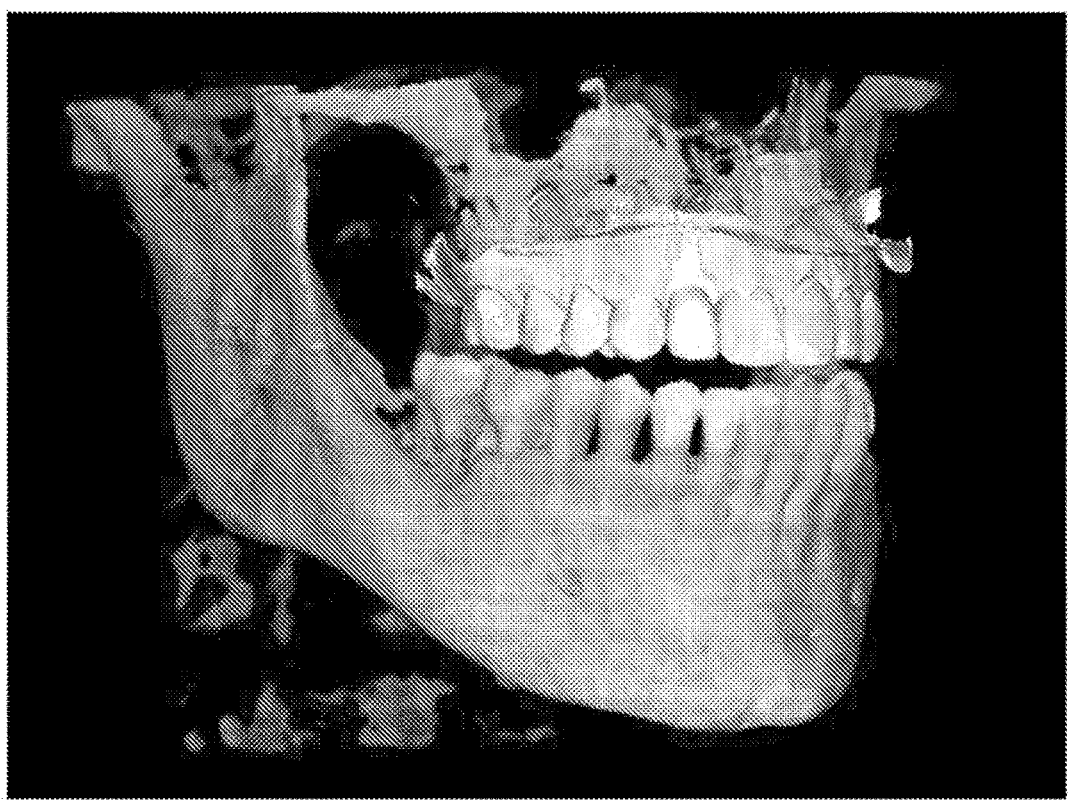
FIG. 26

IRRIGATED SURGICAL GUIDES AND METHODS OF MANUFACTURING THE SAME

CROSS-REFERENCE TO RELATED APPLICATIONS

This application is a U.S. national stage application of International Application No. PCT/US19/21749 filed on Mar. 12, 2019, which claims priority to U.S. provisional application No. 62/682,489 filed on Jun. 8, 2018, and U.S. provisional application No. 62/641,821, filed Mar. 12, 2018, all of which are incorporated herein by reference in their entireties. This application is related to U.S. non-provisional application Ser. No. 16/299,292 filed on Mar. 12, 2019, incorporated herein by reference in its entirety.

FIELD OF THE INVENTION

Embodiments of the present invention relates generally to the fields of surgical guides, and more particularly to surgical guides having one or more routed irrigation channels. Surgical guides can be used in a variety of surgical procedures, including for example, dental surgery, orthopedic surgery and neurosurgery. Systems and methods for manufacturing the surgical guides are also disclosed.

BACKGROUND OF THE INVENTION

Dental implants are one of the most common and effective treatment modalities for the replacement of missing teeth. The success of the implant depends on osseointegration of the bone around the implant. Osseointegration is dependent on several factors, but the most important is the essential primary healing around the dental implant (fusion of bone to the implant surface) [1]. It is vital that the osteotomy preparation not damage the cells during the drilling process in such a manner that might prevent healing. One universal and critical problem associated with implant failure is thermal damage at the drilling site which can cause osteocyte degeneration, hyperemia, fibrosis, necrosis and increased osteoclastic activity, which can all prevent implant osseointegration [2-5]. Heat is generated during implant drilling which can cause some level of necrosis [6]. Very simply, by drilling into the bone, if the heat generation is not limited, the bone will burn, die, and the implant will not integrate.

The current state of the art for implant drilling technology minimizes the heat during the drilling procedure by including sophisticated drill designs, drilling protocols, and coolant delivery systems including internally irrigated hollow drills with irrigation canals through the middle [7]. Most drilling systems however, utilize an external irrigation method in which the irrigation tubing is mounted to the surgical hand piece and the fluid is injected toward the rotating drill, as shown in FIG. 1 below. One factor in this configuration is the fact that most implant companies do not manufacture internally irrigated twist drills for use with their implant product platform. The commercially available implant hand piece shown in FIG. 1 includes a universal tubing setup. This hand piece can be used for internally irrigated drills, or with standard drills (bottom tube). As drilling is completed through a typical surgical guide (shown in FIG. 2), the irrigating fluid from the bottom tube is blocked, rendering it ineffective.

Because of the problems noted above, the usage of surgical guides during implant osteotomy preparation causes a significant increase in temperature compared to non-guided osteotomies and increases the risk of implant failure [7,8]. As noted in the discussion of FIG. 2 above, a typical surgical guide will block the flow of coolant. Numerous studies including those cited above demonstrate that even rapid exposure of the bone to non-irrigated drilling rapidly increases bone temperature, leading to bone necrosis.

Referring now to FIG. 3, standard implant motors typically have an irrigation pump built in. However, these devices are not utilized effectively when used with conventional surgical guides since the irrigation tube extends to the surgical hand piece and fluid is blocked by the guide. U.S. Patent Pub. 2017/0095261 to Strbac et al. describes a bone drilling device having a first internal conduit for supplying coolant directly to the drill and a second external conduit for supplying external coolant to the exterior of the drill via drill openings on the drill guide. The issue with this configuration is that coolant is not directed towards the treatment site. Instead, coolant is directed towards the opening of the drill guide perpendicularly, and thus cannot be properly be directed towards the treatment site. U.S. Pat. No. 5,688,283 to Knapp, U.S. Pat. Pub. 2010/0256649 to Capsal et al., and U.S. Pat. Pub. 2017/0071697 to Groscurth et al. and also describe conventional devices and techniques known in the art.

Still further, guides are conventionally created utilizing a process that can require several visits to a medical suite for a guide that is manufactured at an off-site facility. The inconvenience associated with managing multiple visits and the infrastructure needed to communicate with an off-site facility for generating a single guide make current procedures expensive and inefficient.

What is needed in the art is an improved device and method that can more effectively utilize the irrigation pump built into standard implant motors, allowing for irrigation fluid to effectively reach the target when a surgical guide is being used. Improved systems and methods of creating the surgical guides are also desired.

SUMMARY OF THE INVENTION

In one embodiment, an apparatus for guiding a surgical instrument includes a proximal side and a distal side; a first channel configured to guide a material removal device, wherein the first channel extends from the proximal side of the apparatus to the distal side of the apparatus; and a second channel configured to direct irrigation fluid, wherein the second channel extends from the proximal side of the of the apparatus to the distal side of the apparatus, and wherein the first channel is separate from the second channel. In one embodiment, the second channel is in fluid communication with a plurality of channels that extend to the distal side of the apparatus. In one embodiment, the plurality of channels are positioned around the first channel. In one embodiment, the plurality of channels terminate at discharge ports on the distal side of the apparatus. In one embodiment, the discharge ports are positioned around the first channel. In one embodiment, the plurality of channels are configured to direct irrigation fluid to a surgical site during use. In one embodiment, a coupling mechanism coupled to the proximal side of the apparatus. In one embodiment, the coupling mechanism is in fluid communication with the second channel. In one embodiment, the coupling mechanism is configured to couple to surgical tubing. In one embodiment, the apparatus is configured for use in dental surgery. In one embodiment, the apparatus is configured for use in dental implant surgery. In one embodiment, the apparatus is configured for use in orthopedic surgery. In one embodiment, the apparatus is configured for use in neurosurgery. In one embodiment, the first channel is configured to guide a drill. In one embodiment, the first channel is configured to guide a laser. In one embodiment, the apparatus is formed from an additive manufacturing (AM) process. In one embodiment, the apparatus is formed from a three-dimensional (3D) printing process. In one embodiment, the first channel comprises a first opening on the proximal side, wherein the first opening is configured to receive the material removal device; the first channel comprises a second opening on the distal side, wherein the second opening is proximal to the surgical site when the apparatus is in use; the second channel comprises a first opening on the proximal side, wherein the first opening is configured to receive a source of irrigation fluid; the second channel comprises a second opening on the distal side, wherein the second opening is configured to direct irrigation fluid to the surgical site when the apparatus is in use; the first opening of the first channel is separate from the first opening of the second channel; and the second opening of the second channel is separate from the second opening of the second channel. In one embodiment, a method of performing a surgical procedure includes the steps of placing a guide at a surgical site; directing a material removal device through the first channel to remove material from the surgical site; and directing irrigation fluid through the second channel to provide cooling to the surgical site. In one embodiment, the material removal device is a drill. In one embodiment, the material removal device is a laser. In one embodiment, a third channel is configured to provide fluid communication between the first and second channels.

In one embodiment, a method of manufacturing a surgical guide includes the steps of determining a plurality of parameters for a guide channel in a surgical guide, wherein the guide channel is configured to guide a material removal device; determining a plurality of parameters for an irrigation channel, wherein the irrigation channel is configured to direct irrigation through the surgical guide; and forming the surgical guide with the guide channel and the irrigation channel, wherein the irrigation channel is separate from the guide channel. In one embodiment, forming the surgical guide comprises an additive manufacturing (AM) process. In one embodiment, forming the surgical guide comprises a three-dimensional (3D) printing process. In one embodiment, the plurality of parameters for an irrigation channel comprises a location for a coupling mechanism to couple the irrigation channel to a source of irrigation fluid. In one embodiment, the location for the coupling mechanism is manually selected by a user. In one embodiment, the location for the coupling mechanism is automatically selected by the system. In one embodiment, the plurality of parameters for the irrigation channel comprises locations for discharge ports of the irrigation channel. In one embodiment, the locations for the discharge ports are selected via an automated process executed by a computer processor. In one embodiment, the locations for the discharge ports are manually selected and customized by a user. In one embodiment, the irrigation channel is in fluid communication with multiple channels that terminate at the discharge ports. In one embodiment, the routing of the multiple channels is selected via an automated process executed by a computer processor. In one embodiment, the method includes the steps of imaging a surgical site on a patient to generate patient anatomy data; selecting at least one parameter for manufacturing a surgical guide for use at the surgical site; generating a guide model based on the patient anatomy data and the at least one selected parameter; selecting at least one routed irrigation parameter for implementing a routed irrigation channel on the guide model; and 3D printing a surgical guide based on the guide model and the routed irrigation parameter. In one embodiment, the routed irrigation parameter comprises at least one of a location and an angle of an coupling mechanism to the routed irrigation channel. In one embodiment, the routed irrigation parameter comprises at least one of a location, angle, diameter and number of ejections ports of the routed irrigation channel. In one embodiment, the method includes the steps of receiving patient anatomy data based on imaging a surgical site of a patient; receiving at least one parameter for manufacturing a surgical guide for use at the surgical site; generating a guide model based on the patient anatomy data and the at least one selected parameter; receiving at least one routed irrigation parameter for implementing a routed irrigation channel on the guide model; and generating a signal to 3D print a surgical guide based on the guide model and the routed irrigation parameter. In one embodiment, the routed irrigation parameter comprises at least one of a location and an angle of an coupling mechanism to the routed irrigation channel. In one embodiment, the routed irrigation parameter comprises at least one of a location, angle, diameter and number of ejections ports of the routed irrigation channel.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 3 illustrates a prior art implant motor with an irrigation pump built in.

FIGS. 14A and 14B illustrate a prior art surgical guide.

FIG. 18 is a table of p-value analysis of Experimental v. Control for change in bone temperature and change in drill temperature according to an experimental example.

FIG. 19 is a table of mean, median, and standard deviation of temperature change in bone and osteotomy drill according to an experimental example.

FIGS. 25A and 25B are computer generated images of data sets merged by selecting common point locations on the cbct and intraoral scan allowing a best fit alignment to occur according to an experimental example.

FIG. 26 is a computer generated image of the waxed tooth automatically merged for restorative driven implant placement according to an experimental example.

DETAILED DESCRIPTION OF THE INVENTION

Figure 1:
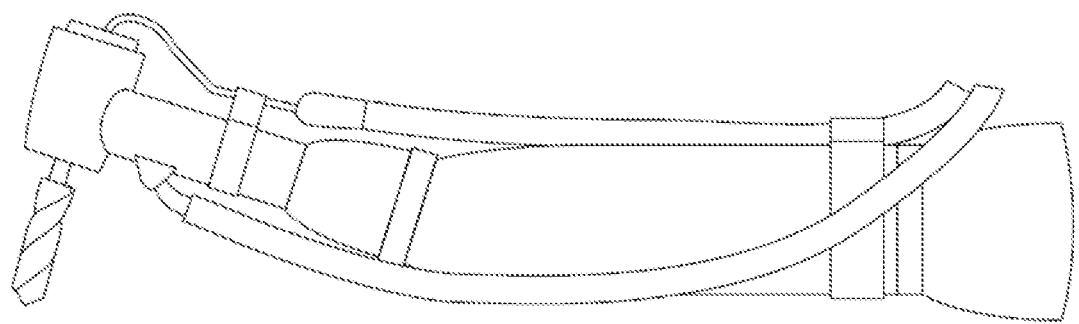
FIG. 1 illustrates a prior art drilling systems utilizing an external irrigation method in which the irrigation tubing is mounted to the surgical hand piece and the fluid is injected toward the rotating drill.
Figure 2:
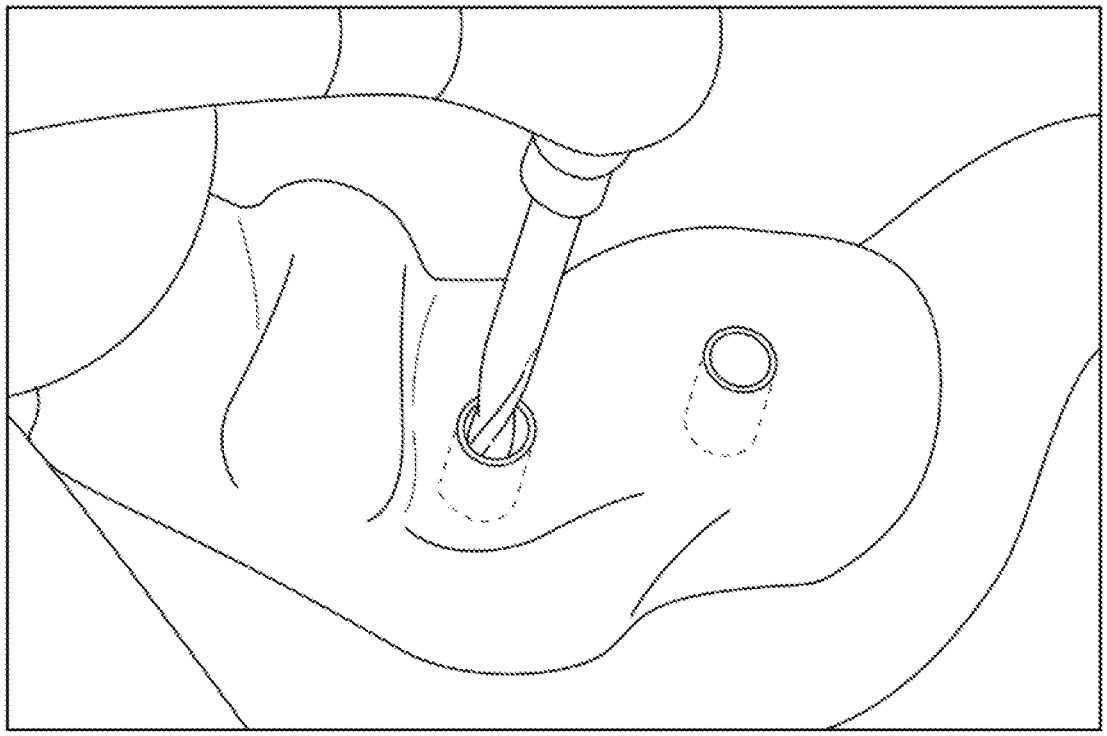
FIG. 2 illustrates a prior art surgical guide in which the irrigating fluid from is restricted during use, rendering it ineffective.
Figure 3:
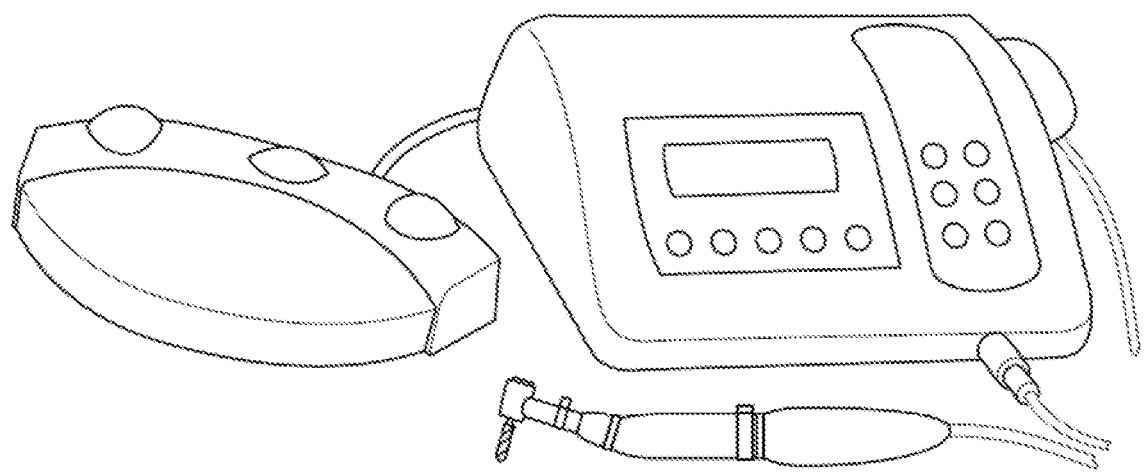

It is to be understood that the figures and descriptions of the present invention have been simplified to illustrate elements that are relevant for a more clear comprehension of the present invention, while eliminating, for the purpose of clarity, many other elements found in surgical guidance systems, methods and devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein are systems, methods and devices for surgical guides having routed liquid coolant irrigation.

Certain embodiments describe a surgical guide that readily allows for internal irrigation and cooling of the bone during implant drilling or other surgical procedures in which heat is generated. In certain embodiments the guide may be manufactured via an additive manufacturing (AM) process, including for example, a three-dimensional (3D) printing process. In certain embodiments, an apparatus and methods are described that include surgical guides with internal channels that can provide irrigation fluid to the surgical site. In certain embodiments, the apparatus and methods include surgical guides with internal channels that can provide irrigation fluid to the surgical site. In typical existing systems, the guide hole through which the drill (or other material removal device) passes creates an intimate fit and no meaningful liquid can pass. Exemplary embodiments of the present disclosure allow the directed passage of the irrigating liquid to the intended site (e.g. where the implant drill engages the bone in certain embodiments). The irrigation ports can be customized and modified for each individual scenario depending on surgical approach, drill angulation, handedness of the surgeon, condition of the patient oral cavity, etc.

Figure 4:
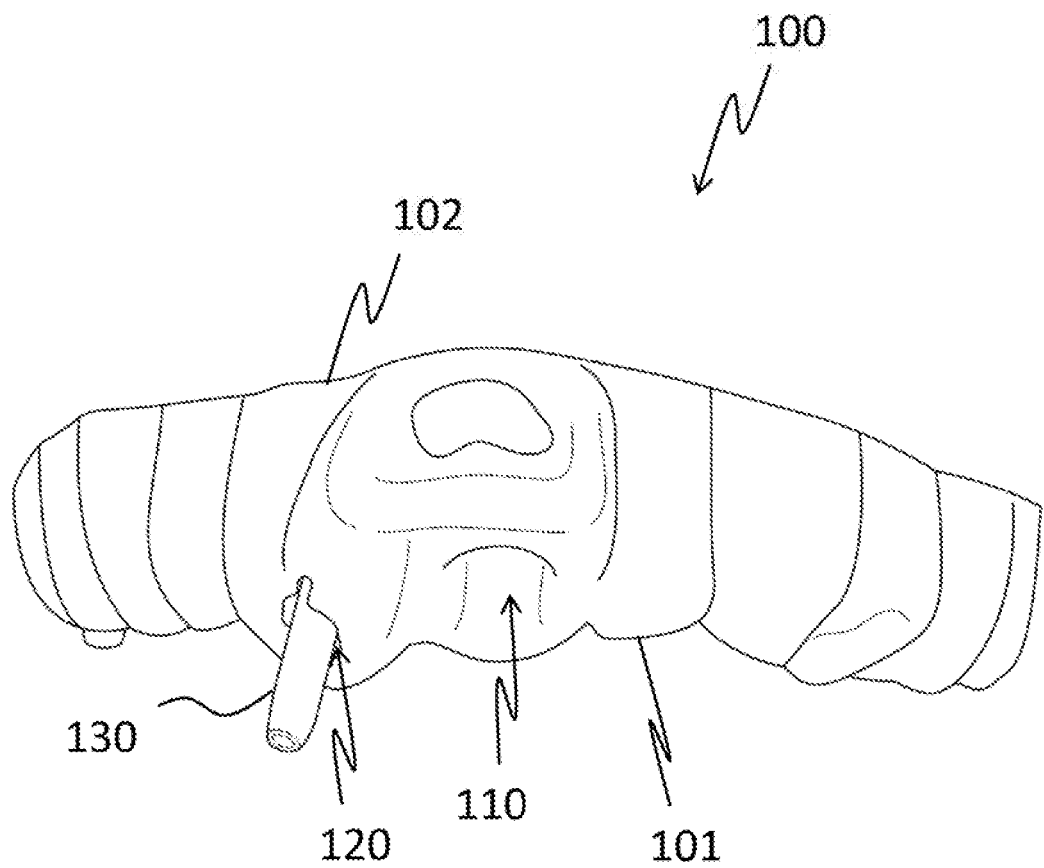
FIG. 4 illustrates a first perspective view of a surgical guide according to an exemplary embodiment of the present disclosure.
Figure 5:
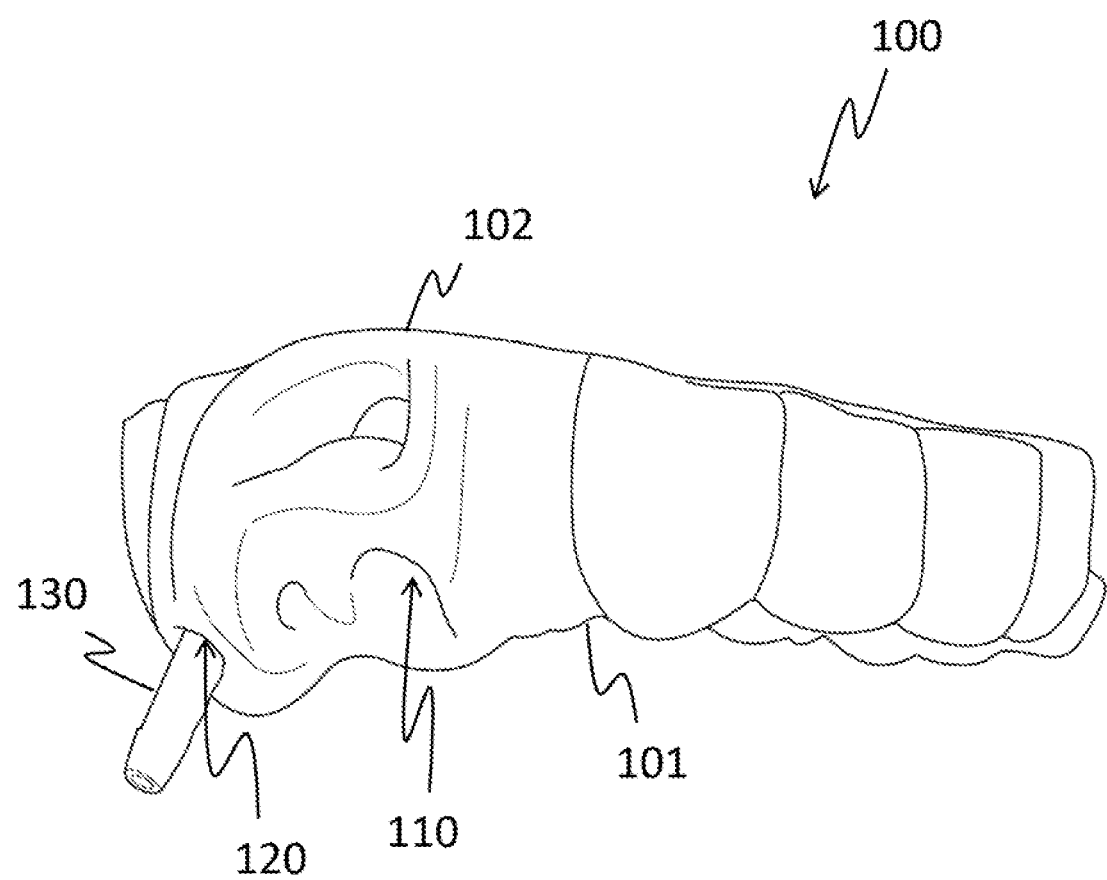
FIG. 5 illustrates a second perspective view of the embodiment of FIG. 4.
Figure 6:
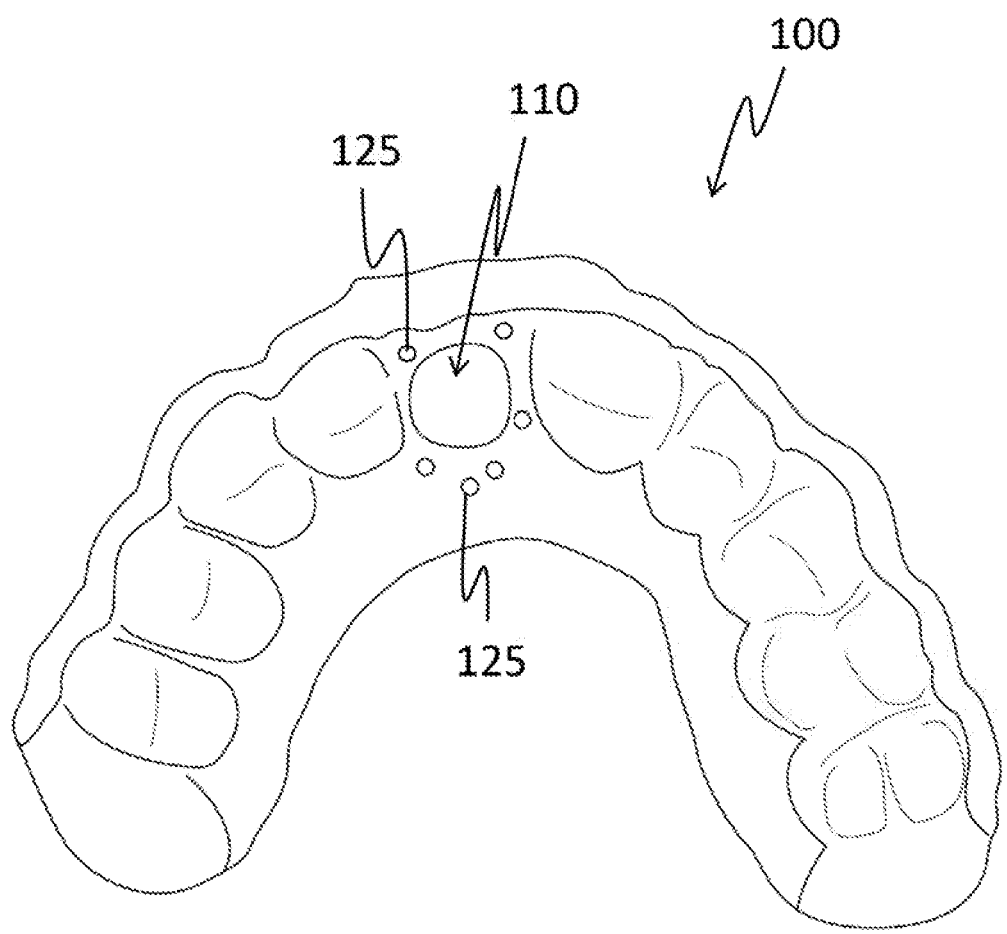
FIG. 6 illustrates an orthographic view of the embodiment of FIG. 4.

Referring now to FIGS. 4 and 5, two perspective views of a surgical guide 100 are shown according to one exemplary embodiment. In this embodiment, surgical guide 100 includes a proximal side 101 and a distal side 102. During use, the proximal side 101 would be positioned toward the surgeon, while the distal side 102 would be positioned toward the surgical site. FIG. 6 illustrates a bottom orthographic view of the distal side 102 of guide 100 which mates with the patient's teeth, soft tissues, and/or bone and faces the surgical site.

The embodiment shown in FIGS. 4-6 comprises a first channel 110 configured to guide a surgical device, such as a surgical material removal device (e.g. a drill, laser, or other device configured to remove material from a surgical site). In addition, surgical guide 100 comprises a second channel 120 configured to direct irrigation fluid to the surgical site. First channel 110 and second channel 120 extend from the proximal side 101 to the distal side 102 of the surgical guide 100. In addition, as shown in the figures, the first channel 110 is separate from the second channel 120. Accordingly, during use, fluid flow will not be restricted if a material removal device is inserted into first channel 110 and creates a close clearance fit between the device and first channel 110. Superior cooling and flushing of debris at the treatment site can be achieved by substantially increasing the flow rate of fluid to the treatment site.

Surgical guide 100 may also comprise a coupling mechanism 130 coupled to proximal side 101. In certain embodiments, the coupling mechanism 130 can be configured to couple to surgical tubing or other suitable conduit, which can also be in fluid communication with a source of irrigation fluid (including for example, an irrigation pump). Accordingly, the source of the irrigation fluid can provide fluid that flows through second channel 120 and is directed to the distal side 102 of surgical guide 101 (e.g. the side of surgical guide 101 proximal to the surgical site).

In certain embodiments, the second channel 120 is in fluid communication with a plurality of channels that branch off and extend to the distal side 102 of the apparatus. This plurality of channels can terminate at discharge ports 125, as shown in FIG. 6. Accordingly, the second channel 120 may begin as a single opening on side 101 (where coupling mechanism 130 is coupled) and branch out into multiple channels that terminate at the distal side 102 of surgical guide 100. In one embodiment, the second channel 120 includes a branch in fluid communication with the first channel 110 so that at least some fluid is supplied directly to the drill via the first channel 110 while simultaneously supplying fluid to the target treatment site. Accordingly, a third channel can be configured to provide fluid communication between the first and second channels.

In particular embodiments, discharge ports 125 are positioned around at least a portion of the perimeter of the first channel 110, which can aid in distributing and directing the irrigation fluid to the surgical site during use in a more uniform or targeted fashion. This configuration can help to reduce or minimize any temperature increase in the tissue at the surgical site during the surgical procedure, particularly temperature increases due to friction when a drill is used to remove material during the procedure.

In certain embodiments, total irrigation flow rates to the target treatment site are provided at the rate of 50 ml per minute, 100 ml per minute, 200 ml per minute, 300 ml per minute, 500 ml per minute, 750 ml per minute, 1,000 ml per minute, 1,500 ml per minute, 2,000 ml per minute or more. In one embodiment, total irrigation flow rates to the target treatment site are maintained between 50 ml per minute and 2,000 ml per minute during active drilling. In one embodiment, total irrigation flow rates to the target treatment site are maintained between 100 ml per minute and 2,000 ml per minute during active drilling. In one embodiment, total irrigation flow rates to the target treatment site are maintained between 500 ml per minute and 2,000 ml per minute during active drilling. In one embodiment, total irrigation flow rates to the target treatment site are maintained between 750 ml per minute and 2,000 ml per minute during active drilling. In one embodiment, total irrigation flow rates to the target treatment site are maintained between 1,000 ml per minute and 2,000 ml per minute during active drilling. In one embodiment, total irrigation flow rates to the target treatment site are maintained between 1,500 ml per minute and 2,000 ml per minute during active drilling. In one embodiment, flow rates described above are maintained for a period of time before and/or after active drilling to flush and clear debris from the treatment site and to further maintain low temperatures. In one embodiment where the device has multiple discharge ports, each discharge port maintains total irrigation flow rates above 50 ml per minute during active drilling. In one embodiment where the device has multiple discharge ports, each discharge port maintains total irrigation flow rates above 100 ml per minute during active drilling. In one embodiment where the device has multiple discharge ports, each discharge port maintains total irrigation flow rates above 300 ml per minute during active drilling. Generally, multiple discharge ports can collectively provide total irrigation flow rates to the target treatment site according to the ranges provided above.

In certain embodiments, the surgical guide 100 can be manufactured or formed via an additive manufacturing (AM) process, including for example, a three-dimensional (3D) printing process. In particular embodiments, certain aspects of the design of surgical guide 100 may be selected via an automated process executed by a computer processor. For example, a user may select a location of an opening on the proximal side 101 in which second channel 120 begins (e.g. the location of coupling mechanism 130). The automated computer aided design (CAD) process can then determine the optimal routing of channel 120 through surgical guide 100 and determine the location of one or more discharge ports 125.

As noted previously, while certain figures and descriptions of the exemplary embodiments included herein are directed to a dental application, embodiments of the invention may include other types of surgical guides and is not limited to dental applications. For example, similar guided drilling protocols exist for orthopedic surgery and neurosurgery and other embodiments of the invention may be applied in such applications.

Figure 7:
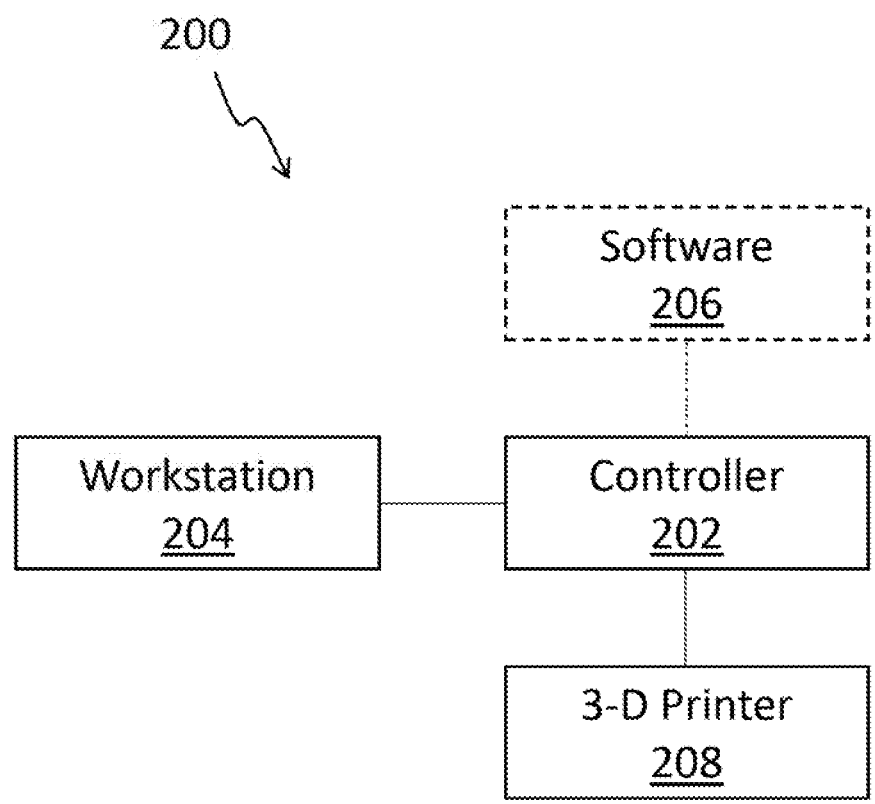
FIG. 7 is a system diagram for a surgical guide manufacturing system according to one embodiment.

With reference now to FIG. 7, a system 200 for manufacturing a surgical guide is shown according to one embodiment. The system 200 includes a controller 202 such as a computer that is connected to a workstation 204. The workstation 204 can be a separate computer such as a laptop or handheld smart device, and can include inputs such as a keyboard and mouse, and outputs such as a display. The workstation 204 can also communicate with medical equipment such as imaging devices including scanners, which may specifically include 3D intraoral scanners or 3D CBCT scanners. The controller 202 communicates with software resident in the system, or software 202 on a remote server or cloud. The software 202 is designed to implement the embodiments described in further detail below. The controller 202 is also in communication with a 3D printer for producing the finished surgical guide device.

Figure 8:
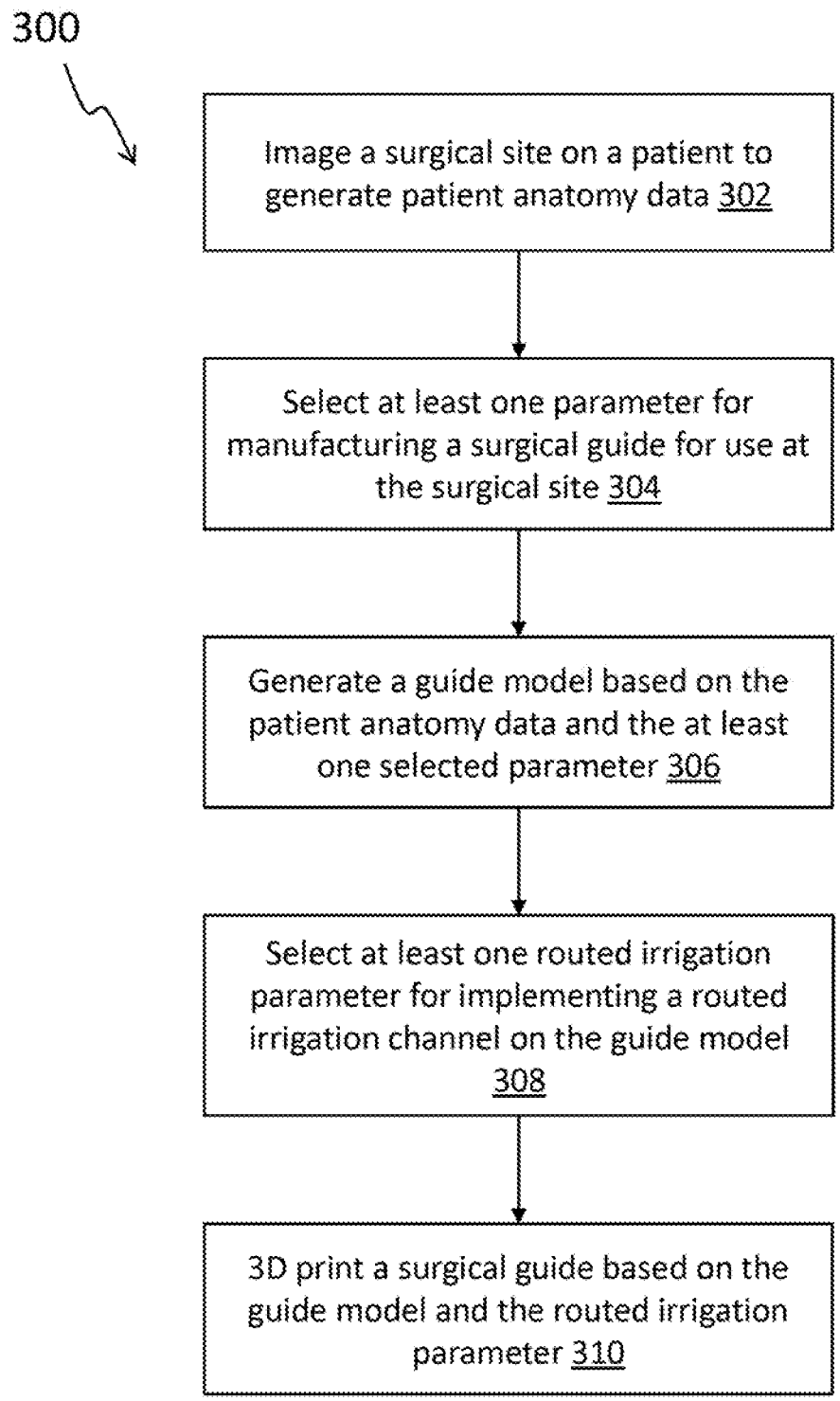
FIG. 8 is a flowchart of a method of manufacturing a surgical guide according to one embodiment.
Figure 9:
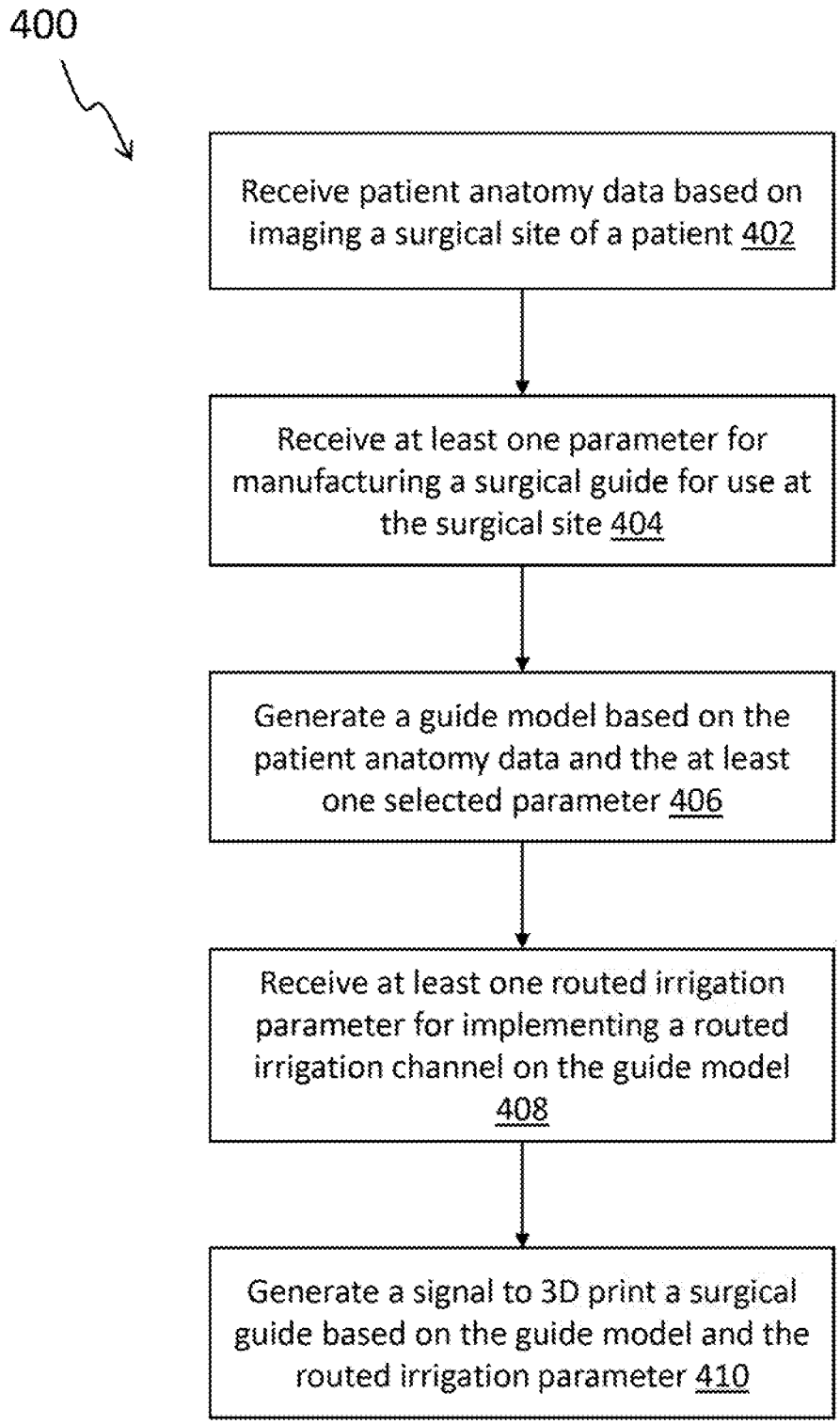
FIG. 9 is a flowchart of a method of manufacturing a surgical guide according to one embodiment.

With reference now to FIG. 8, a method for 3D printing a surgical guide is shown according to one embodiment. A surgical site on a patient is imaged to generate patient anatomy data 302. At least one parameter is selected for manufacturing the surgical guide that will be used at the surgical site 304. A guide model is generated based on the patient anatomy data and the at least one selected parameter 306. At least one routed irrigation parameter is selected for implementing a routed irrigation channel on the guide model 308. The surgical guide is then 3D printed based on the guide model and the routed irrigation parameter. Accordingly, a service provider can offer medical professionals the ability to efficiently and cost-effectively print customized 3D surgical guides on-site by providing a system with these capabilities. According to one embodiment 400 with reference now to FIG. 9, the system implements the steps of receiving patient anatomy data based on imaging a surgical site of a patient 402, receiving at least one parameter for manufacturing a surgical guide for use at the surgical site 404, generating a guide model based on the patient anatomy data and the at least one selected parameter 406, receiving at least one routed irrigation parameter for implementing a routed irrigation channel on the guide model 408, and generating a signal to 3D print a surgical guide based on the guide model and the routed irrigation parameter 410. Accordingly, surgical guides according to embodiments described herein can be 3D printed in office using technology such as software, 3D printers, and FDA cleared resins known in the art.

An exemplary embodiment of a system for manufacturing 3D printed surgical guides will now me described in more detail. First, the system will merge a 3D intra-oral scan and virtually designed tooth (waxup) with the patient's 3D CBCT scan using best fit algorithms or common data points, then the system will virtually place a 3D rendering of the desired implant on the CBCT/scan into an ideal position referencing the bone, adjacent anatomy, and tooth waxup. Next, the implant sleeve is added. Utilizing the guide design module, the system will set the path of insertion/draw of the guide, define the area that you want covered by the guide, and create custom parameters for thickness of the guide. This may include space between guide and the teeth, gap to sleeve space, and guide sleeve housing thickness (can alter wall thickness, inner diameter, outer diameter, height, and distance to implant, etc.). Next, software creates a model of the guide based off the implant plan and custom parameters defined above.

Next, post rendering edits can be implemented. This may include adding holes in the guide via remove material button (the holes are usually added to verify that the guide will seat clinically). Addition of these holes which pass completely through the guide can be created for passage of irrigant from the surgical handpiece through the guide to the drilling site. Users may alter the extent of the guide flange which can be useful for surgical approach and guide seating, but also potentially important for how the routed irrigation could be designed. The physical extent of the guide can support irrigation tubing, entrance and exit ports, etc. The extended flange extension will also allow or inhibit the flow or irrigation fluid at the crest of the ridge or bone and can be customized. Users may add a solid bar of material to reinforce weak areas or to add guide material to supply mass for routing or supporting the irrigation tubing or porting.

Next, the guide is reimported back into the implant planning module to check for fit and to verify guide design on the hard and soft tissues. The user can add guide irrigation at this point, and the .stl file can be imported to CAD software. Then, the steriolithography STL of the surgical guide file is exported from the software. Users can select the location and angle of the coupling mechanism on the exterior of the guide. The coupling mechanism can be strategically placed at a position and angle to allow for convenient access but also to prevent it from interfering with the surgical instrumentation. The entrance position can be placed sufficiently away from the implant drilling site, but also at an angle to allow emergence of the port and therefore the irrigation tubing to avoid surgical interference and avoid kinking of the tubing on the oral tissues. For example, when planning an implant on an upper-arch front tooth site, a right-handed surgeon may choose to place the irrigation coupling mechanism 2-3 teeth sites to the operator's right. The emergence of the port/tubing can likewise be directed to the right and in an occlusal direction to allow passive emergence of irrigation tubing out of the patient's mouth (not bind the opposing arch, cheek, or other oral tissues, but also be out of the way). Alternatively, another example would be for a right handed surgeon operating on the patient's right side may want the coupling mechanism and tubing emerging entirely on the opposite of the guide/arch to remain out of the way.

The user may then design the coupling mechanism parameters. The coupling mechanism parameters can be customized, for example, customizing port internal diameter, external diameter, method of tube or connector retention, and length. These can all be customized to match the tubing compatible with the operator's implant system to create a water and pressure tight connection, or allow flexibility to be compatible with any connection from other tubing, syringe, or pump systems. Alternatively, rather than creating port compatible with existing tubing systems, this new technology may justify the use of a novel quick connector, which could be more user friendly. The port parameters can also be relative to the ideal physical properties of the printed guide material, meaning that the design can be customized to reduce risks of mechanical failure of narrow fragile ports, especially for brittle resin materials.

Next, the user may define the locations and parameters associated with the ejection ports. This is intended to direct the irrigation coolant fluid to allow maximum reduction of heat development to the osteotomy drills. The use can add exit (ejection) ports to the hollow channel area near the location of the drilling site and guide sleeve to provide irrigation. Because of differences in each site with respect to implant drilling diameter, site width, soft-tissue interference, hard tissue interference, the following parameters can be customized. The number of ports and position of ports around the guide site can be defined based upon the anatomy of the edentulous site(s), the exposure of the site (whether the guide flanges extend short of, to, or beyond the tissue surfaces), and whether circumferential or unidirectional liquid flow is desired. For maximum cooling, irrigation from all directions may be appropriate, however, unidirectional irrigation may allow more efficient outflow of the irrigant from one side to be expelled or suctioned from another and could offer superior cooling and flushing of the site. This may be dependent upon how open the surgical site is, whether it's is effectively sealed by the guide (gap from guide to tissue or not), whether the tissue is surgically reflected, and how the surgical assistant intends to suction fluid away from the site.

The angle of the ports/irrigation ejection can be customized to allow direct cooling of the drill. Irrigation should be directed at the exposed drill as close as possible to the bone or tissue surface while drilling. The angle and pressure should also allow flushing of the flutes of the twist drills to efficiently remove drill debris. This indirectly reduces the risk of drilling thermal trauma and decreased the need to stop the procedure to physically clear the drill. Angulation can also factor in the changes in ideal position and angulation of irrigation based upon sequential drilling with drills of different sizes and diameters given an implant systems protocol. I.e. different ports can be directed in different positions and angles to account for all the drill steps. The sum of all the planned ports can account for these intended variations.

Extension of the ports from the guide can be customized to account for distance from the guide to the tissue surfaces (i.e. if the distance from the designed guide to tissue surface is significant-gapped, extensions can be added to allow more direct cooling flow). Also, the extensions can be designed to route around interferences like protrusions from adjacent teeth, or the soft tissues, or can account for intentional future changes made like flap design and tissue reflection.

Further, the diameter of the ejection ports, and the internal and external diameters of any extensions can be defined to control fluid spray rate/pressure to the drills. This can also be dependent upon the pump force settings of the pumping or syringing system used to push the irrigant and these parameters can be matched.

Various criteria can be relied upon to determine how specific ejection parameters are assigned or determined? In one example and according to one embodiment, if the treatment involves surgically reflecting the tissue, the ideal angulation can be approximately defined from the ejection port to the center of the osteotomy at the crest of the bone. Alternatively, in another example and according to another embodiment, for a flapless case, the ideal angulation can be from the ejection port to the center of the osteotomy as it penetrates the soft tissue.

The locations and parameters associated with the integrated guide tubing can be defined. As the entrance of the irrigation, and the exit are designed, tubing to connect the entrance and exit ports must be created. The design strategy can be customized to allow for a more streamlined digital/coding workflow, and to allow for ideal travel of fluid through the guide. There are different ways to create this tubing, all of which can be automated. Bulk material can be created from the coupling mechanism to the exit ports to effectively thicken a channel through or on the guide, including a hollow channel through the bulked material to permit the flow of liquid from the coupling mechanism to the exit port(s), the width, length and route of this channel can be modified. Surface mounted tubing can also be created from the entrance site to the ejection ports intimately mounted to the guide's surface contours and/or creating straight line tubing across the surface irregularities of the guide.

If multiple exit port sites are utilized due to a guide intended to be used for multiple implant sites, a valve system can be created that allows redirection of irrigation to different sites as the surgeon works on each site.

The option for connection of suction to the guide can also be implemented. In cases that are totally enclosed, where the flange of the guide extends to the soft tissue surfaces, outflow of irrigation to the site may be blocked. This may reduce the efficiency of irrigation. This problem can be balanced with the addition of outflow channels. These outlets could allow passive exit of fluid, or could be routed to clinical suction tubing. This could facilitate flushing of fluid and debris from the site. Suction could connect directly to the surgical site area, or could be routed around the guide (like the irrigation tubing), to allow for a convenience. The connector port could be customized with respect to diameter, length, etc. to allow direct connection to a practitioner's system. Or could justify the creation of a new tubing system to connect from the clinician's operatory system to the guide. A semi-rigid but bendable narrower diameter than a normal saliva ejector intended to be connect to the surgical guide for this purpose via a port can be utilized.

Once the guide is designed, it will need to be printed. Some of the above parameters may entail physical details beyond the clinician's 3D printing resolution on their equipment. The workflow could be customized per the practitioner's equipment to allow effective printing. For example, the resolution of the 3D printer can be set at 100 microns or greater. Some of the fine details of the guide could be physically expanded to facilitate successful 3D printing. Alternatively, the internal routing and diameter can be altered for resins with a propensity for clogging or rapid internal curing. Embodiments of the guide can be formed from additive manufacturing or 3D printing. In one embodiment, surgical guides are milled from monolithic blocks or materials.

Figure 10:
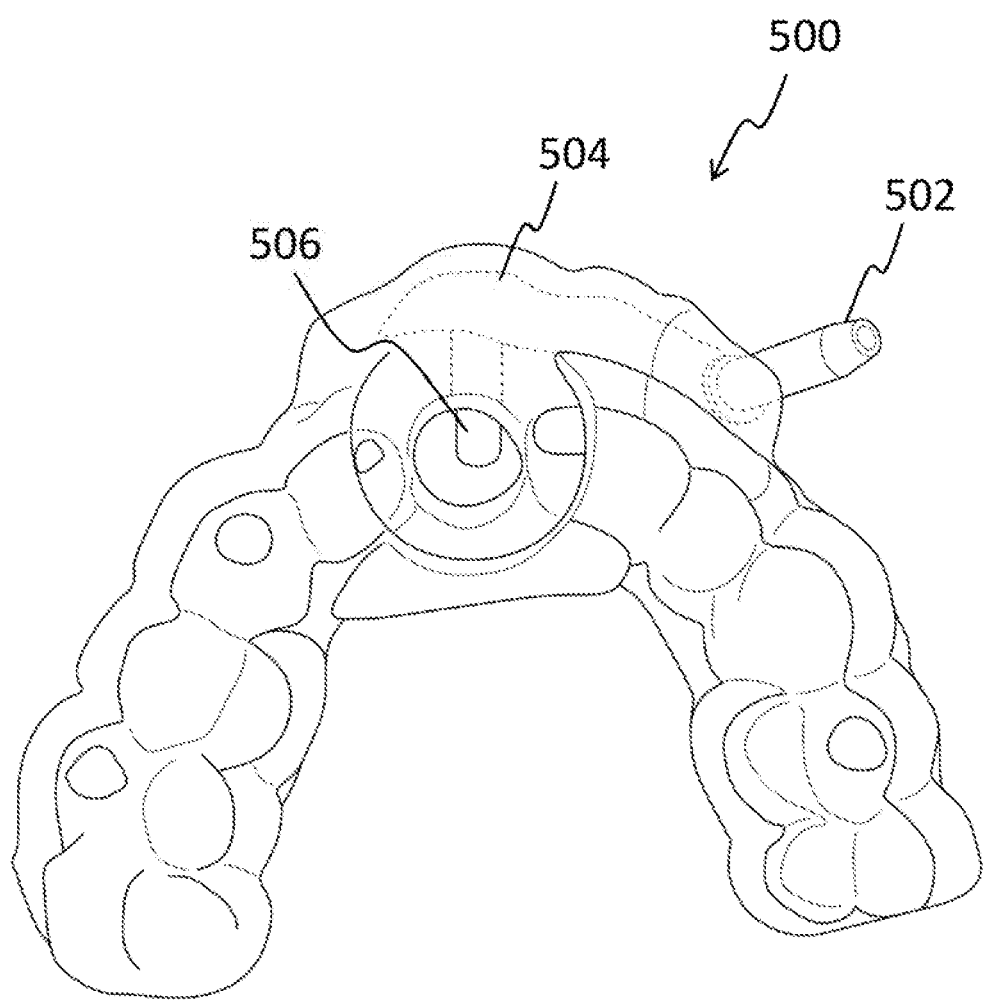
FIG. 10 is a perspective view of a surgical guide according to one embodiment.

Embodiments of the guide can include holes for the verification of seating, a sleeve housing to fit the metal sleeve, and bars for structural support. With reference now to the guide shown in FIG. 10, the guide 500 can include coupling mechanisms 502 for tubing and irrigant entrance, and internal custom canals 504 that carry irrigation solution from the coupling mechanism 502 to the ejection ports 506 at the site of the osteotomy. The ejection ports 506 allow guided cooling around the drill site to ensure application and flow of irrigation solution at the surgical site.

Figures 11A, 11B, 11C:
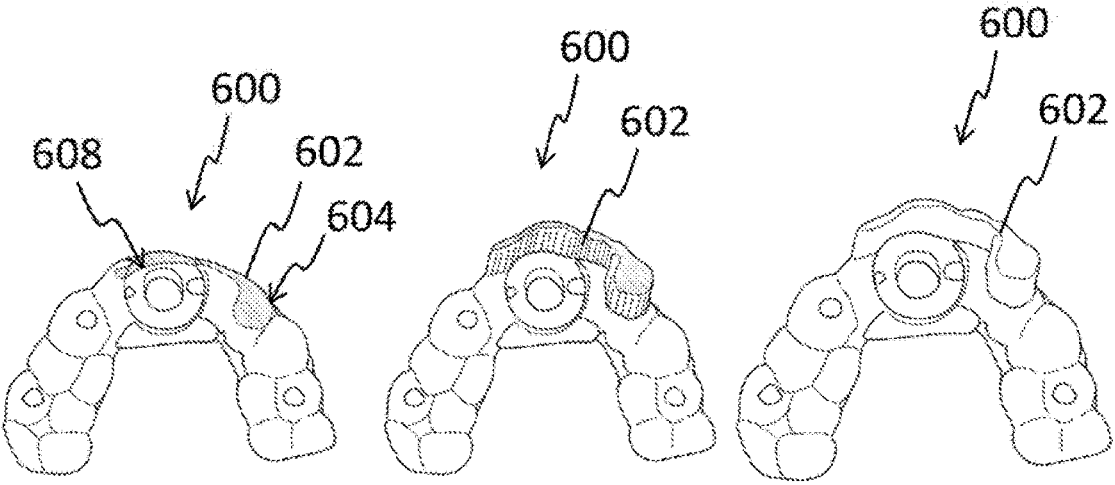
FIGS. 11A-11F are perspective views of a surgical guide illustrating steps of a manufacturing process according to one embodiment.
Figures 11D, 11E, 11F:
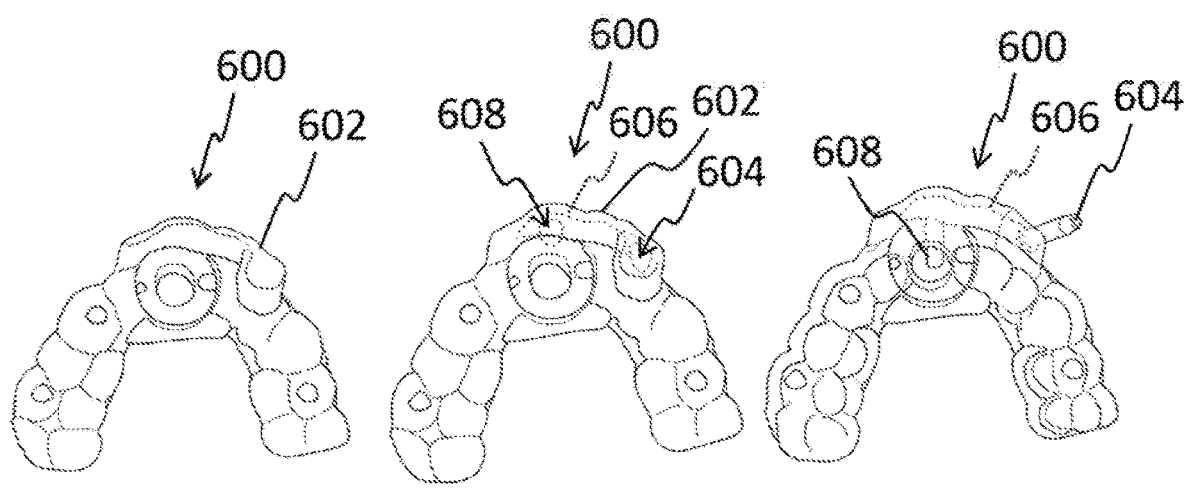
Figure 12A:
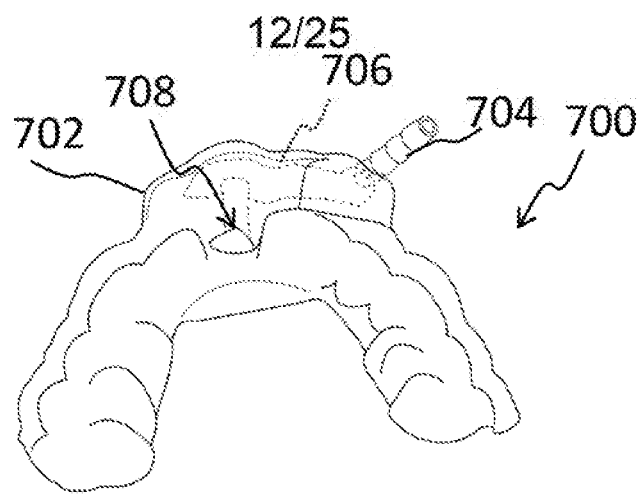
FIGS. 12A-12C are alternate perspective views of a surgical guide according to one embodiment.
Figure 12B:
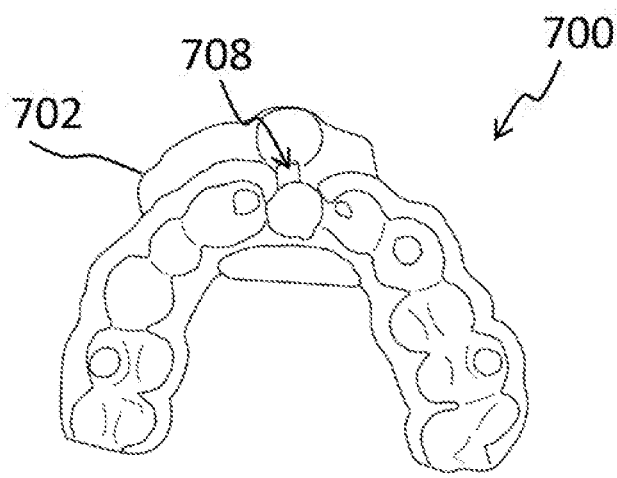
Figure 12C:
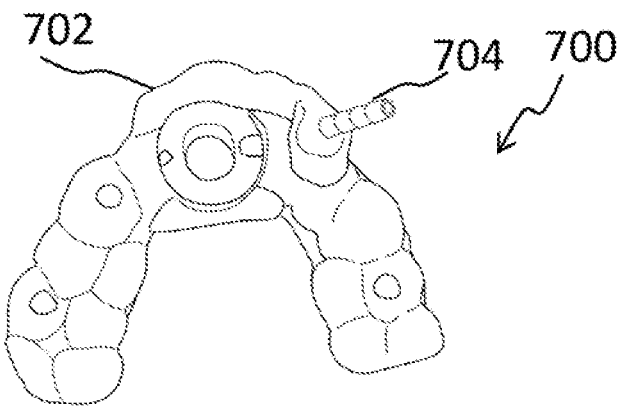

With reference now to the embodiments shown in FIGS. 11A-11F, embodiments of a surgical guide device 600 are shown, according to steps in a manufacturing process. The location from the coupling mechanism(s) 604 to the ejection port(s) 608 is selected manually or automatically avoiding critical structures and interferences with normal fit and function of the guide 600 (FIG. 11A). Material 602 is added to ensure the irrigation channel 606 will be water tight and strong while allowing adequate flow of material to the directed sites (FIG. 11B). The material is then smoothed and virtually added to the guide (FIG. 11C). The material is smoothed and virtually added to the guide which can now receive the irrigation tube (FIG. 11D). A water tight tube 606 is created in the thickened material that provides a tunnel from the future coupling mechanism 604 to the ejection ports 608 (FIG. 11E). Finally, an coupling mechanism 604 is connected to the irrigation tube 606 which will carry irrigation from the source of origin into the irrigation tube 606 (FIG. 11F). These can be custom made to fit various sources of irrigation. FIGS. 12A-12C are alternate perspective views of a surgical guide 700 that can be manufactured according to the methods described herein according to one embodiment. The guides 700 include an coupling mechanism 704 and exit port 708 connected by an irrigation channel 706 manufactured from a material 702 forming the irrigation channel 706.

Figure 13A:
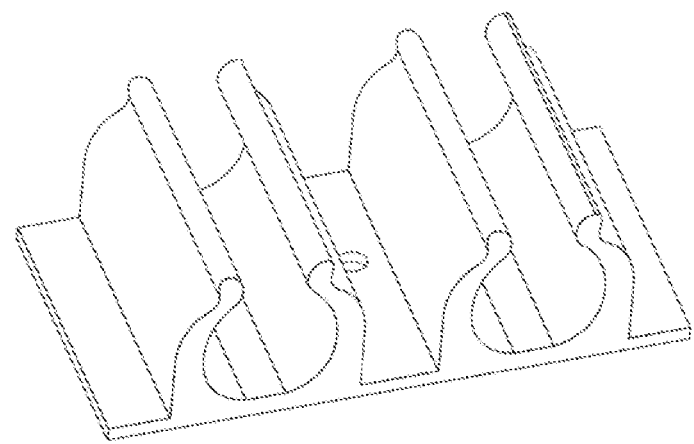
FIGS. 13A and 13B are embodiments of clips that can be integral to or attached to the surgical guide for securing fluid tubing to the surgical guide.
Figure 13B:
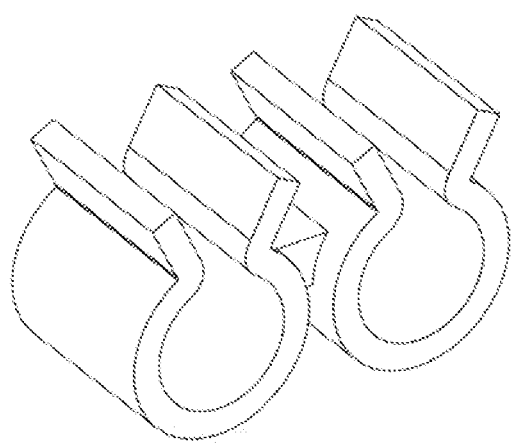

With reference now to FIGS. 13A and 13B, in one embodiment, instead of internal irrigation tubes, a 3D printed pathway for the surgical irrigation tubing to be routed can be created. In one embodiment, it is the surgical tubing taking the liquid to the site via tubing that is routed through tubing attachment mechanisms on the surgical guide, such as the clips shown in FIGS. 13A and 13B. The clips allow the user to bend the tubing while keeping it securely attached to the surgical guide to follow the selected path to the surgical site. Tubing can be connected to predefined or customized fluid ports along the surgical guide for customizing fluid delivery and pathways.

Figure 14C:
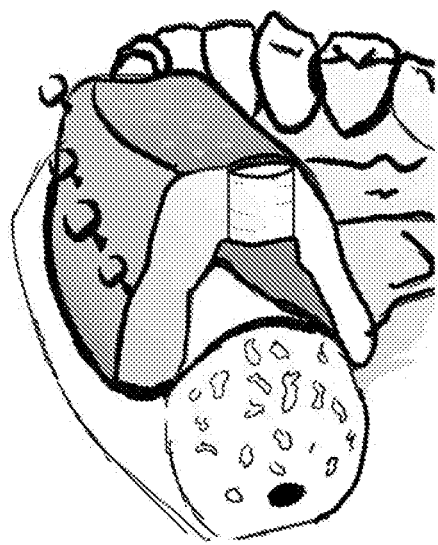
FIGS. 14C-14F illustrate embodiments of surgical guides with fluid tubing according to alternate embodiments.
Figure 14D:
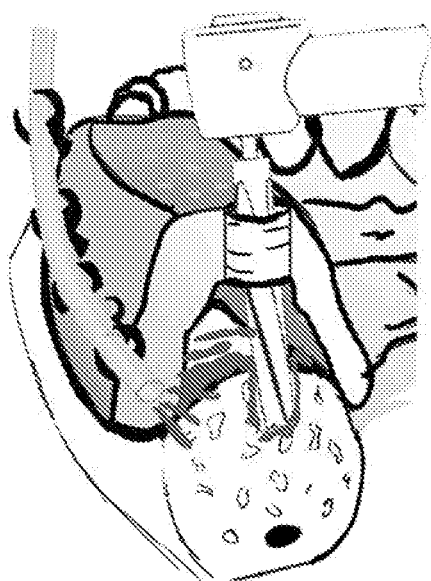
Figures 14E, 14F:
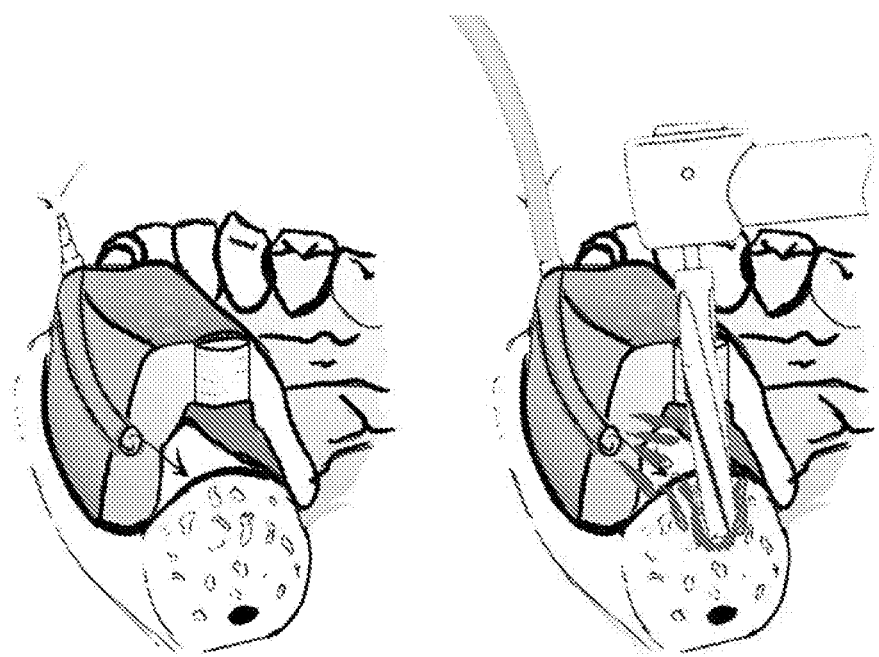

As illustrated now in FIGS. 14A and 14B as explained above, the current state of the art does not provide for water irrigation to cool the bone as the surgical guide blocks the flow of irrigation solution. With reference now to the embodiments shown in FIGS. 14C-14F, clips and other types of attachments can be added to the guide design to rout irrigation tubing or any other vehicles for cooling liquid to the drilling site. Custom irrigation channels can be added within the guide with attachment coupling mechanisms to route tubing and irrigation through the guide to ejection ports around the drilling site. The irrigation tube can also be on the surface of the guide rather than through the internal aspect of the guide, or it can traverse both. The system and method described above can be implemented to optimally place clips, coupling mechanisms and ejection ports accordingly on the manufactured surgical guide accordingly.

While this invention has been disclosed with reference to specific embodiments, it is apparent that other embodiments and variations of this invention may be devised by others skilled in the art without departing from the true spirit and scope of the invention. For example, embodiments described herein can be applied to various parts of the body and for various parts of the body, including but not limited to dental implants, oral implants, maxillofacial implants, and medical implants.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Experiments were conducted to determine if embodiments of an irrigation system 3D printed into the surgical guide will cause a decrease in temperature in the bone during osteotomy preparation compared to the bone temperature during conventional surgical guide osteotomy preparation. Experiments were also conducted to demonstrate the technique on a patient with a clinical case.

Material and Methods

Figure 15:
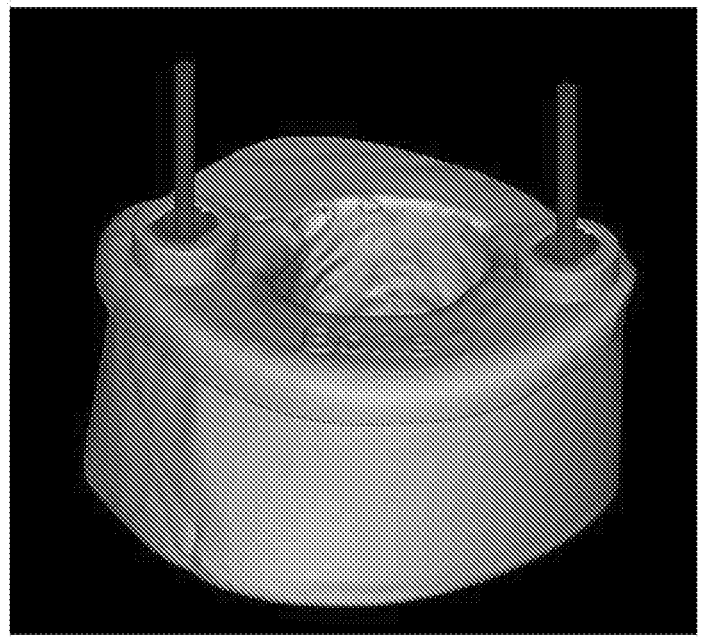
FIG. 15 shows a computer generated image of a surgical guide according to an experimental example.
Figure 16:
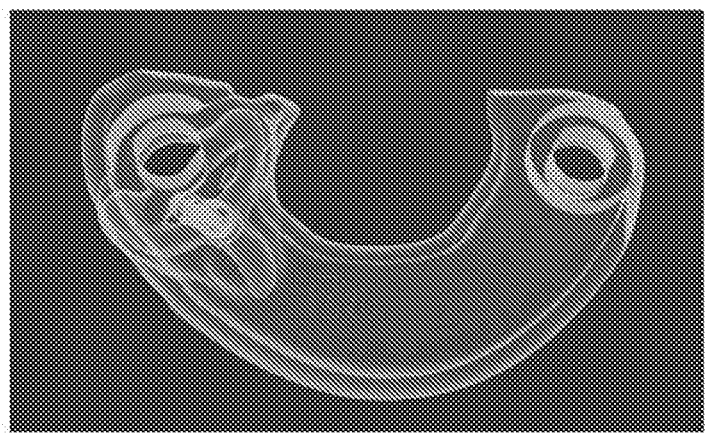
FIG. 16 shows a computer generated image of a surgical guide after adding a custom irrigation canal to one of the guide tubes according to an experimental example.

Five fresh bovine shin bones were harvested and scanned with CBCT (Promax Mid; Planmeca). The rationale for choosing bovine cortical bone is that both human and bovine cortical bones are thermally isotropic and therefore there is no need to use human cortical bone [9]. The CBCT scans were then converted into stereolithography (STL) files using the integrated STL file export feature in digital design software (Romexis; Planmeca). From the converted files, 3D surgical guides were designed on 3D (Romexis; Planmeca) guide software. Each of the five guides was then digitally designed with two surgical guide sleeves (Stecco) to accommodate surgical osteotomy preparation for appropriate implant system (Astra Osseospeed EV 4.2×9 mm; Denstply Sirona) (FIG. 15). Prior to printing, each of the five guides was imported into custom design software (Autodesk Meshmixer) to design custom irrigation canals to one of the implant sites as the experimental group (FIG. 16). The site selected to receive the custom irrigation canals was selected at random. During the digital fabrication of custom irrigation canal, one of the surgical guide tubes in each guide was left unaltered to serve as the control group. Once modified, each guide was 3D printed (Form 2; Formlabs) using surgical guide resin (Dental SG; Formlabs).

The fit of each surgical guide was verified on each bone and the bones were then modified to accommodate use of temperature recording devices. Prior to modification, the surgical guides were utilized, along with pilot drill (Osseospeed EV; Dentsply Sirona), to guide pilot hole placement into each bone for both experimental and control side. Pilot holes served as a reference for the modifications which were made along the vertical axis of implant placement. To accommodate the K type thermocouplers (3M) the axial wall of the bones were prepared with two retainer holes at 3 mm and 6 mm from the crestal height of the ridge respectively. A 4×4×4 mm window was also cut into axial wall at 9 mm from the crestal height of the ridge, the depth of osteotomy placement, to allow for live temperature reading of dental drill by thermal video camera (E8; FLIRE). All modifications were made using a dental highspeed handpiece (Timax Z 40:1; NSK) and a straight, cross-cut fissure surgical bur. All measurements were made with periodontal probe (Michigan "0" probe; Hu-Friedy) from crestal height of the bone.

Figure 17:
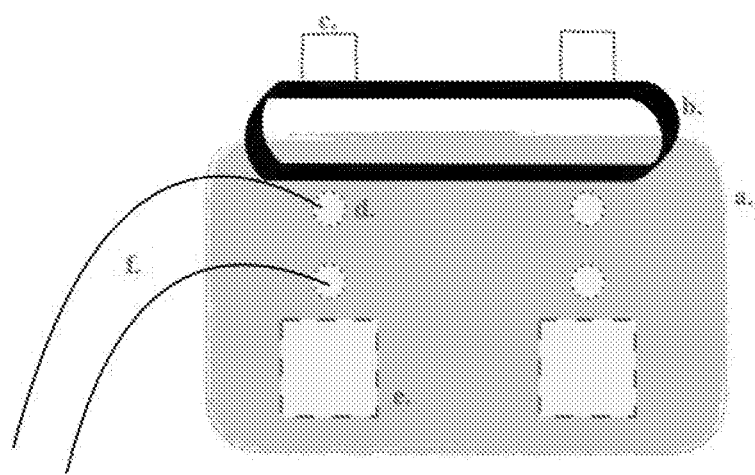
FIG. 17 shows a diagram of an experimental setup according to an experimental example (Legend: a—axial view of bone, b—surgical guide, c—guide tube, d—thermocoupler retainer, e—4×4 mm window for live thermal imaging, f—thermocoupler. Note: Parafilm placed between "a" and "b".)

Five modified bovine bones were then placed into thermal bath to standardize temperature prior to performing experiment. Each bone was taken out of the thermal bath immediately prior to osteotomy preparation. The crestal portion of the bones, to which the guide was fitted, was covered with Parafilm to simulate gingival deflection of irrigant seen in the intra-oral environment. The Guide was placed over the Parafilm to secure it in place. K-Type thermocouplers (3M) were then glued and taped into retainer sites created at 3 mm and 6 mm. (FIG. 17) K-type thermocouplers were connected to digital thermometer (Digital Thermocouple Thermometer Dual Channel; Proster) to record temperature readings. Osteotomy was performed at each site (experimental and control guide sleeves) using two successively larger drills in appropriate sequence for implant system (Astra Osseospeed EV; Denstply Sirona) at 1,500 rpm in surgical contra-angle dental handpiece (Ti-max X SG20L; NSK). Highest temperature readings were recorded from digital thermometer (Digital Thermocouple Thermometer Dual Channel; Proster) during each drill for both experimental and control groups. At final depth of osteotomy preparation, the thermal camera (E8; FLIRE) was used to capture live thermal image of drill tip.

Results

Temperature change in bone, recorded with K-type thermocouplers (3M), of the experimental group was significantly lower than the temperature change seen in the control group (Table 1, FIG. 18). The experimental group exhibited a mean temperature change of 7.13 degrees for the first osteotomy drill and 3.70 degrees for the second osteotomy drill (Table 2, FIG. 19). While the control group demonstrated a 25.54 degree mean temperature change in the first osteotomy drill and a 14.14 degree mean temperature change in the second osteotomy drill. Both experimental and control groups demonstrated higher standard deviation in bone temperature change for the first osteotomy drill (5.89 experimental/15.33 control) compared to the second osteotomy drill (3.42 experimental/10.53 control).

Figure 20:
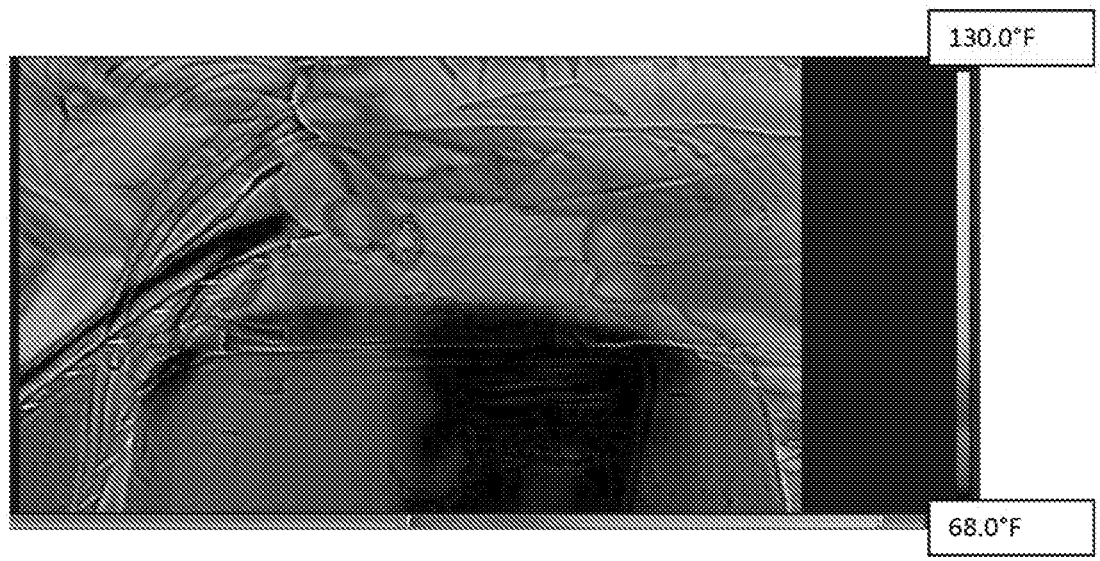
FIG. 20 is an image of a live thermal reading captured by E8 FLIRE thermal video camera according to an experimental example. ("Sp1" reading of 88.0 degrees Farenheit shows temperature of drill tip at final depth of osteotomy preparation in one experimental group.)
Figure 21:
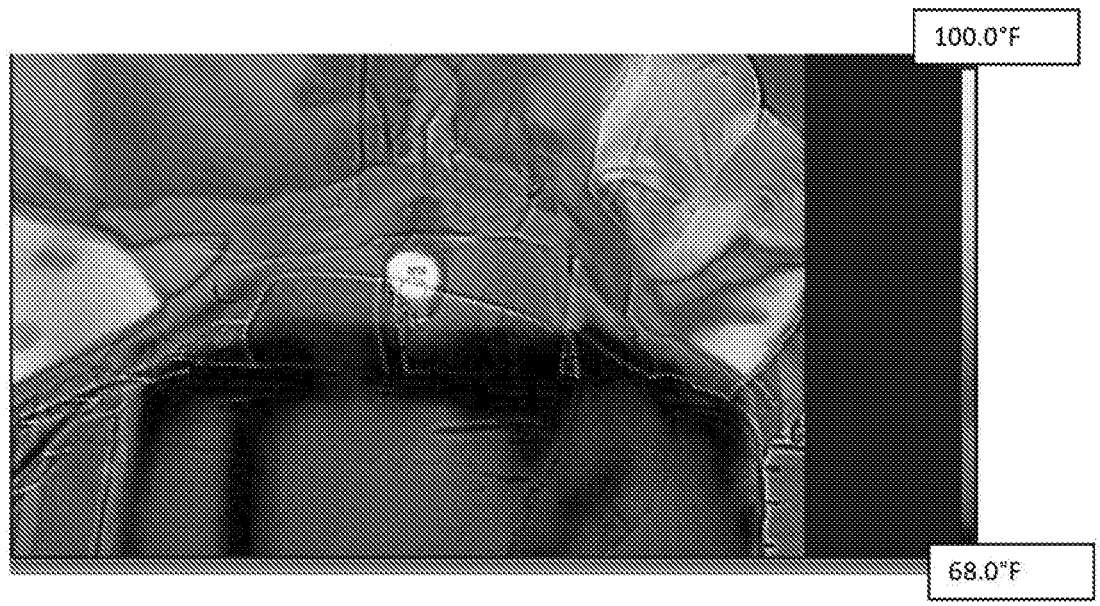
FIG. 21 is an image of a live thermal reading captured by E8 FLIRE thermal video camera according to an experimental example. ("Sp1" reading of 134.5 degrees Farenheit shows temperature of drill tip at final depth of osteotomy preparation in one control group.)

Drill temperature results were recorded as shown in FIGS. 20 and 21 with the live thermal video camera (E8; FLIRE).

The tip of the drill was selected once it dropped into the 4×4 mm window of the bone and the hottest point was selected for each bone. The experimental group demonstrated lower mean change in drill temperature and smaller standard deviation (Mean: 4.18 degrees/Std dev: 4.94) compared to control (Mean: 17.20 degrees/Std dev: 7.76).

Discussion

Current research demonstrates that the osteotomy preparation involved in the placement of dental implants generates some level of heat; which may hinder the successful osseointegration of the dental implant [2-6]. The issue of controlling heat generation while placing dental implants is of critical importance to the field of implant dentistry in order to consistently obtain successful outcomes. Research has shown that utilization of a surgical guide during implant placement significantly increases the temperature of the bone and may lead to implant failure [7, 8]. The results of this study address the issue of heat generation associated with the use of a surgical guide both clinically and in vitro, demonstrating the efficacy of custom designed irrigation canals in surgical guides to curb the rise in bone temperature during guided osteotomy preparation.

Custom irrigation canals designed in the surgical guides significantly reduced the temperature increase of bovine bone associated with drilling of first osteotomy drill. The results from this in vitro and case presentation study address the issue of reducing temperature increase in bone associated with surgical guide usage in vivo. The irrigation from our custom designed irrigation canals was able to reduce the mean temperature increase in bovine bone from 25.54 degree mean temperature change in the control group (no irrigation canal) to 7.13 degree mean temperature change in the experimental group (custom irrigation canal). The significant reduction in temperature change of bone associated with drill 1 as opposed to the insignificant reduction associated with drill 2 seen in our study, may be due to the fact that drill temperature decreases with increasing drill size [10]. The experimental group of osteotomy drills also showed a lower standard deviation compared to our control group. Overall the custom irrigation channels of the experimental group were able to better thermally regulate the bone throughout the osteotomy procedure.

Data recorded with live thermal video camera (E8; FLIRE) demonstrates a significant reduction in drill temperature change associated with custom irrigation channels. Thermal damage in bone begins at 116 degrees Fahrenheit and thus cooling the osteotomy drill is of the utmost importance when trying to control temperature of the surrounding bone and prevent thermal damage [11]. Thermal readings from live thermal camera demonstrate poor thermoregulation of drill in the control group as compared to experimental group. The results from our experiment show that drill temperature can be better regulated with the use of custom irrigation channels embedded in the surgical guides.

The results of this study demonstrate the efficacy of custom designed surgical guides with embedded irrigation canals to significantly reduce osteotomy drill temperature (Table 1, FIG. 18) and stifle the temperature increase of bone during osteotomy. Potential weaknesses of this study may need to be improved in future research of this topic. There was trouble retaining the thermocouples in the pinholes and controlling depth of insertion of thermocouples into the axial wall of the bone. This could have caused slight inconsistency in bone temperature readings. Improved accuracy may result from determining a method to standardize depth of insertion of the thermocouples as well as improving stability in the retainer hole. Osteotomies were placed by human operator and there exists the possibility that the pressure applied when drilling differed slightly, even though all other variables stayed the same. Slight increases or decreases in pressure may have led to variability in temperature change of the bone and the osteotomy drill. Setting up a protocol to monitor pressure applied during drilling may lead to increased consistency in future attempts to test this method. Our study provides evidence of an effective method for increasing thermal regulation of osteotomy drill and surrounding bone temperature. Further research will be necessary and standardized protocols should be developed to determine what method of irrigant delivery is most effective in regulating thermal change in bone.

Case Presentation

Figure 22:
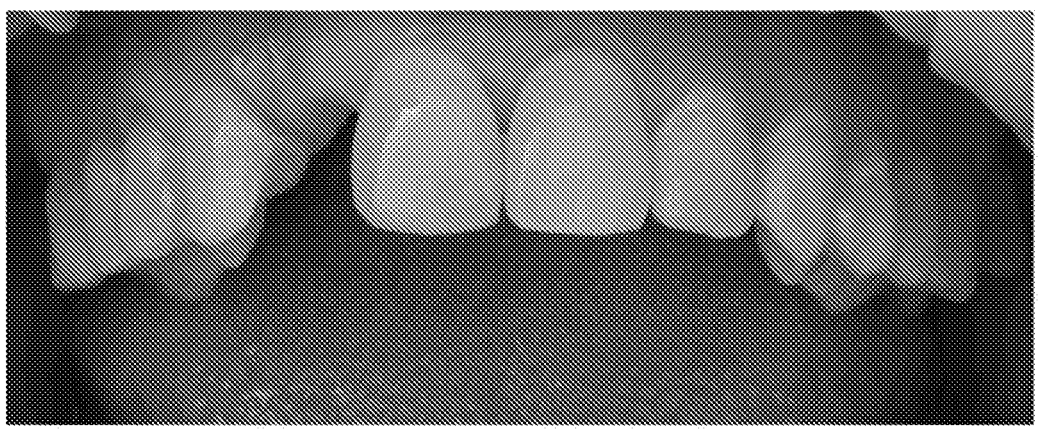
FIG. 22 is an image of a patient edentulous area at site number 7 according to an experimental example.
Figure 23:
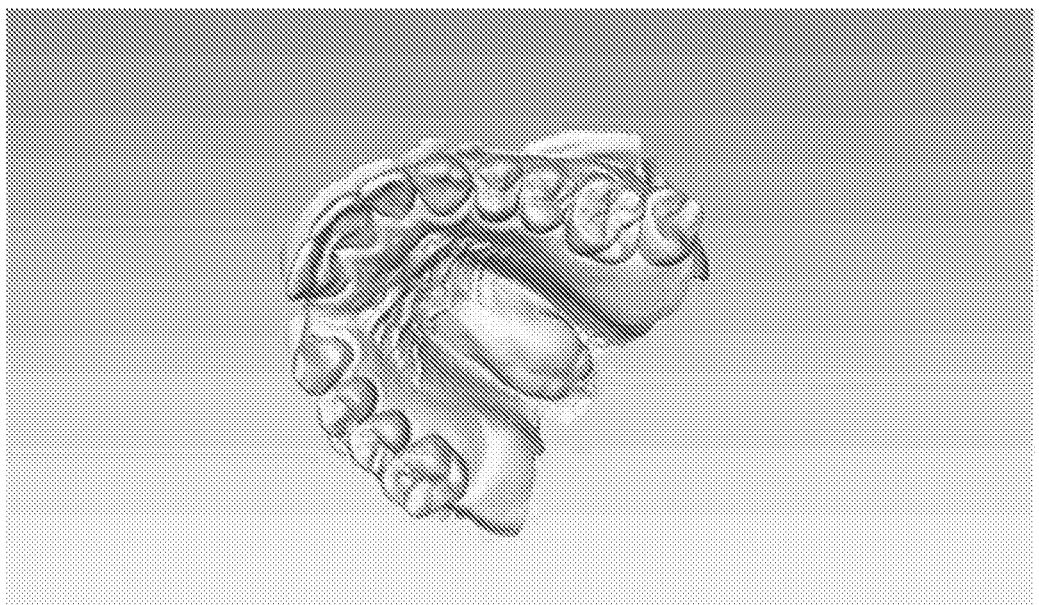
FIG. 23 is a computer generated image of a complete arch intraoral scan according to an experimental example.
Figure 24:
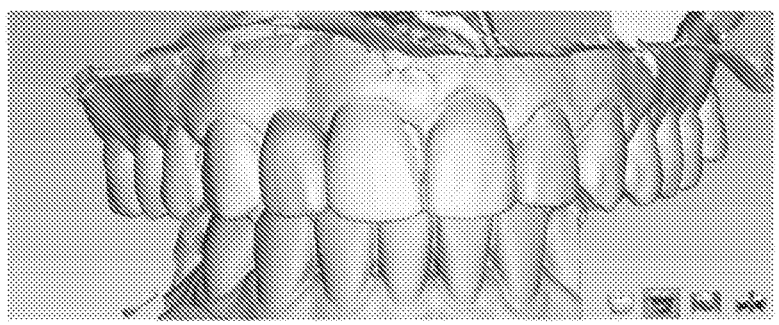
FIG. 24 is a computer generated image of a missing tooth was digitally waxed (Plancad Easy; Planmeca) using a mirror image of the contralateral incisor according to an experimental example.
Figure 27:
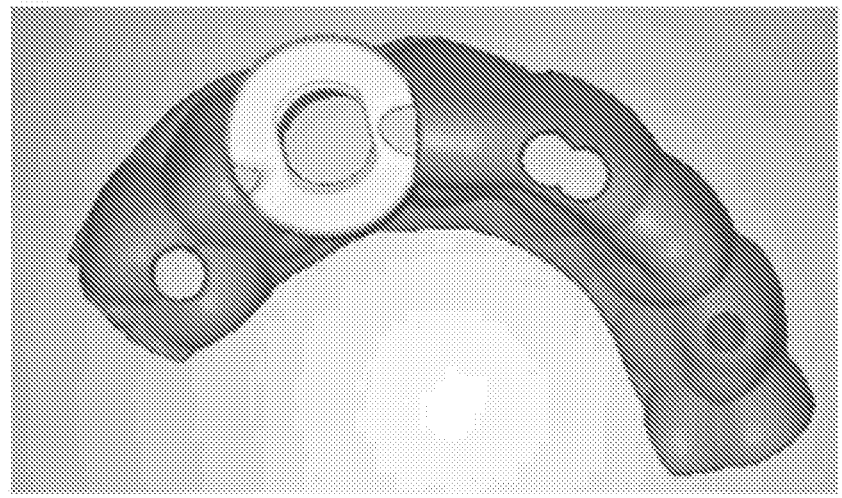
FIG. 27 is a computer generated image of a surgical guide according to an experimental example.
Figure 28:
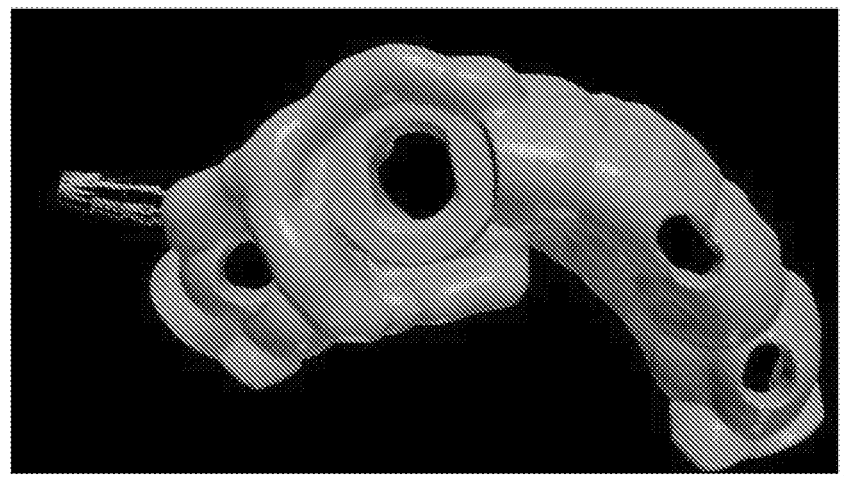
FIG. 28 is a computer generated image of a surgical guide with custom irrigation canals added according to an experimental example.

A 45 year old female presented with an edentulous area at site number 7 (FIG. 22). An Ultra Low Dose CBCT scan was made of the patient (Promax Mid; Planmeca) followed by a complete arch intraoral scan (Emerald; Planmeca) (FIG. 23). The missing tooth was digitally waxed (Plancad Easy; Planmeca) using a mirror image of the contralateral incisor (FIG. 24). The data sets were merged in Romexis (Planmeca) by selecting common point locations on the cbct and intraoral scan allowing a best fit alignment to occur (FIGS. 25A and 25B). After alignment, the waxed tooth was also automatically merged for restorative driven implant placement (FIG. 26). An Astra Osseospeed EV (Dentsply Sirona) was planned with the addition of a Stecco sleeve. Romexis software was used to design the surgical guide and it was exported as an STL file (FIG. 27). The guide was then imported into meshmixer and custom irrigation canals were designed (FIG. 28). The modified guide was then printed (form 2. Formlabs) using dental SG resin. The guide was post processed using manufacturer recommended protocols.

Figure 29:
FIGS. 29 and 30 are images of the guide being checked for proper fit and irrigation flow according to an experimental example.
Figure 30:
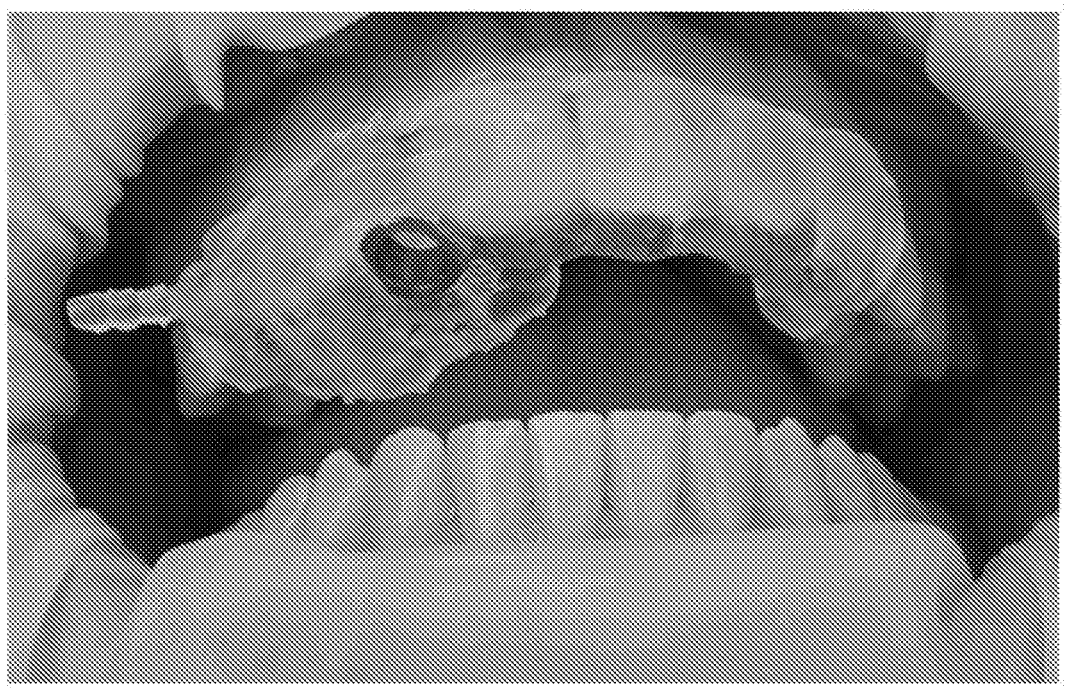
Figure 31:
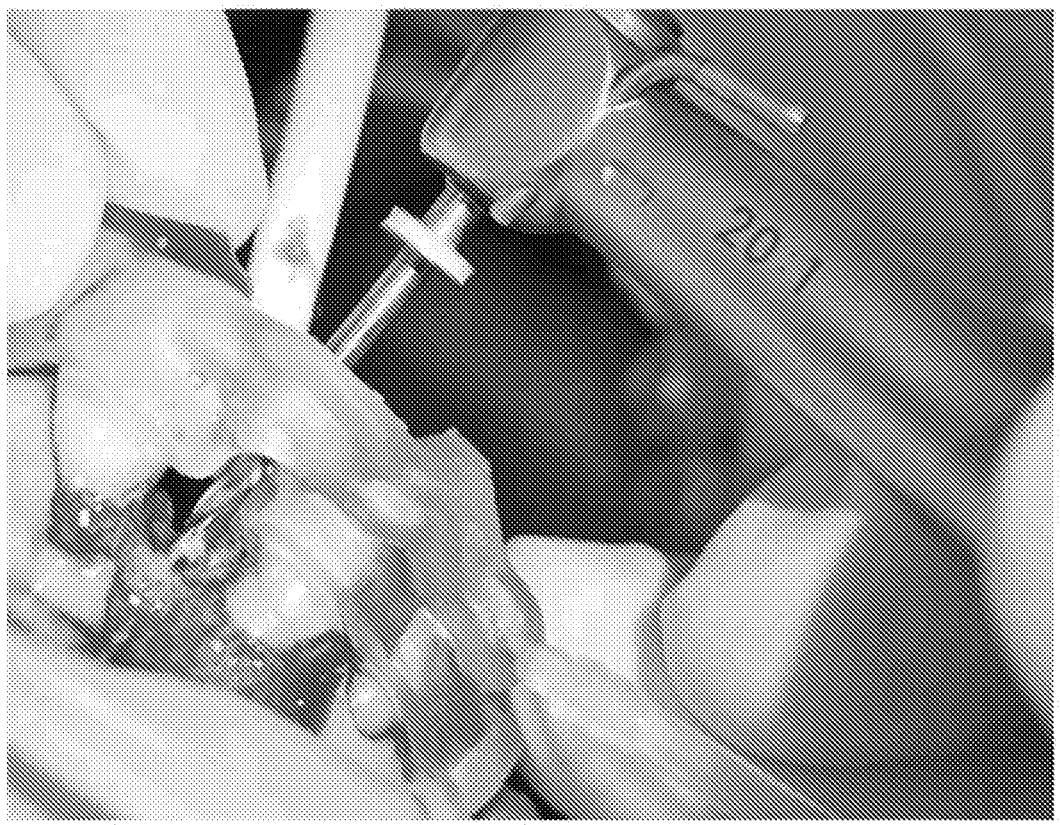
FIG. 31 is an image of osteotomies being made using the custom irrigation ports as the sole source of cooling according to an experimental example.

On the day of surgery, the guide was checked for proper fit and the irrigation tube was attached and checked for flow (FIGS. 29 and 30). The osteotomies were made using the custom irrigation ports as the sole source of cooling (FIG. 31).

CONCLUSIONS

Based on the findings from this pilot study, the following conclusions were drawn: (1) A significant difference appears between experimental group and control group in the ability to control the change in bone temperature during first osteotomy drill (D1) and ability to limit temperature change of osteotomy drill. (2) There is an insignificant difference in temperature reduction between experimental and control for the second osteotomy drill (D2). (3) Custom designed irrigation canals may reduce amount of temperature change seen in bone and drill during 3D static guided osteotomy preparation. (4) This technique can be used successfully on a patient The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

REFERENCES

The following references, to the extent that they provide exemplary procedural or other details supplementary to those set forth herein, are specifically incorporated herein by reference:

1. Albrektsson T, Branemark PI, Hansson H A, Lindstrom J. Osseointegrated titanium implants. Requirements for ensuring a long-lasting, direct bone-to-implant anchorage in man. Acta Orthop Scand 1981; 52:155-70.
2. Eriksson R A, Adell R. Temperatures during drilling for the placement of implants using the osseointegration technique. J Oral Maxillofac Surg 1986; 44:4-7.
3. Kerawala C J, Martin I C, Allan W, Williams E D. The effects of operator technique and bur design on temperature during osseous preparation for osteosynthesis self-tapping screws. Oral Surg Oral Med Oral Pathol Oral Radiol Endod 1999; 88:145-50.
4. Harris B H, Kohles S S. Effects of mechanical and thermal fatigue on dental drill performance. Int J Oral Maxillofac Implants 2001; 16:819-26.
5. Sener B C, Dergin G, Gursoy B, Kelesoglu E, Slih I. Effects of irrigation temperature on heat control in vitro at different drilling depths. Clin Oral Implants Res 2009; 20:294-8.
6. Sharawy M, Misch C E, Weller N, et al: Heat generation during implant drilling: The significance of motor speed. J Oral Maxillofac Surg 60:1160, 2002
7. Scott E S E Bulloch. Comparison of heat generation between internally guided (cannulated) single drill and traditional sequential drilling with and without a drill guide for dental implants. The International journal of oral & maxillofacial implants 27(6) 2012 November-December 1942-4434.
8. Misir A F, Sumer M, Yenisey M, Ergioglu E. Effect of surgical drill guide on heat generated from implant drilling. J Oral Maxillofac Surg 2009; 67:2663-8.
9. Davidson S R, James D F: Measurement of thermal conductivity of bovine cortical bone. Med Eng Phys 22:741, 2000.
10. Soldatos, N et al: Temperature changes during implant osteotomies utilizing 3 different implant systems. The Journal of Implant and Advanced Clinical Dentistry 8(6), 2016 November
11. Mishra S K, Chowdhary R: Heat Generated by Dental Implant Drills During Osteotomy—A Review J Indian Prosthodont Soc. 2014 June; 14(2): 131-143.

What is claimed is:

1. A method of manufacturing a surgical guide, the method comprising:
    determining a plurality of parameters for a guide channel in a surgical guide, wherein the guide channel is configured to guide a material removal device;
    determining a plurality of parameters for an irrigation channel, wherein the irrigation channel is configured to direct irrigation through the surgical guide; and
    forming the surgical guide with the guide channel and the irrigation channel, wherein the irrigation channel is separate from the guide channel.

2. The method of claim 1 wherein forming the surgical guide comprises an additive manufacturing (AM) process.

3. The method of claim 1 wherein forming the surgical guide comprises a three-dimensional (3D) printing process.

4. The method of claim 1 further comprising:
    imaging a surgical site on a patient to generate patient anatomy data;
    selecting at least one parameter for manufacturing a surgical guide for use at the surgical site;
    generating a guide model based on the patient anatomy data and the at east one selected parameter;
    selecting at least one routed irrigation parameter for implementing a routed irrigation channel on the guide model; and
    3D printing a surgical guide based on the guide model and the routed irrigation parameter.

5. The method of claim 4, wherein the routed irrigation parameter comprises at least one of a location and an angle of a coupling mechanism to the routed irrigation channel.

6. The method of claim 4, wherein the routed irrigation parameter comprises at least one of a location, angle, diameter and number of ejections ports of the routed irrigation channel.

7. The method of claim 1 further comprising:
    receiving patient anatomy data based on imaging a surgical site of a patient;
    receiving at least one parameter for manufacturing a surgical guide for use at the surgical site;
    generating a guide model based on the patient anatomy data and the at least one parameter for manufacturing a surgical guide,
    receiving at least one routed irrigation parameter for implementing a routed irrigation channel on the guide model;
    generating a signal to 3D print a surgical guide based on the guide model and the routed irrigation parameter.

8. The method of claim 7, wherein the routed irrigation parameter comprises at least one of a location and an angle of a coupling mechanism to the routed irrigation channel.

9. The method of claim 7, wherein the routed irrigation parameter comprises at least one of a location, angle, diameter and number of ejections ports of the routed irrigation channel.

10. The method of claim 1 wherein the plurality of parameters for an irrigation channel comprises a location for a coupling mechanism to couple the irrigation channel to a source of irrigation fluid.

11. The method of claim 10 wherein the location for the coupling mechanism is manually selected by a user.

12. The method of claim 11 wherein the plurality of parameters for the irrigation channel comprises locations for discharge ports of the irrigation channel.

13. The method of claim 12 wherein the locations for the discharge ports are selected via an automated process executed by a computer processor.

14. The method of claim 13 wherein the irrigation channel is in fluid communication with multiple channels that terminate at the discharge ports.

15. The method of claim 14 wherein routing of the multiple channels is selected via an automated process executed by a computer processor.

* * * * *